United States Patent
Stone et al.

(10) Patent No.: US 10,586,318 B2
(45) Date of Patent: Mar. 10, 2020

(54) AUTOMATED MODEL-BASED INSPECTION SYSTEM FOR SCREENING ELECTRONIC COMPONENTS

(71) Applicant: Raytheon Company, Waltham, MA (US)

(72) Inventors: Kristen Stone, Lowell, MA (US); Alexandra Cintron-Aponte, Pinellas Park, FL (US); Blair Simons, St. Petersburg, FL (US)

(73) Assignee: Raytheon Company, Waltham, MA (US)

( * ) Notice: Subject to any disclaimer, the term of this patent is extended or adjusted under 35 U.S.C. 154(b) by 199 days.

(21) Appl. No.: 15/288,245

(22) Filed: Oct. 7, 2016

(65) Prior Publication Data

US 2018/0101945 A1 Apr. 12, 2018

(51) Int. Cl.
*G06T 7/00* (2017.01)

(52) U.S. Cl.
CPC .. *G06T 7/0004* (2013.01); *G06T 2207/10116* (2013.01); *G06T 2207/30148* (2013.01)

(58) Field of Classification Search
CPC ........... G01N 21/956; G01N 21/95607; G01N 2021/95615; G01N 21/95623; G01N 2021/9563; G01N 2021/95638; G01N 2021/95646; G01N 2021/95653; G01N 2021/95661; G01N 2021/95669; G01N 2021/95676; G01N 21/95684; G01N 21/95692; G06T 7/00; G06T 7/0002; G06T 7/0004; G06T 7/0006; G06T 7/0008;

(Continued)

(56) References Cited

U.S. PATENT DOCUMENTS 6,324,298 B1 * 11/2001 O'Dell ............... G01N 21/9501
257/E21.53
6,791,339 B2 9/2004 Licini et al.
(Continued)

FOREIGN PATENT DOCUMENTS

DE 10-2010-011066 9/2011

OTHER PUBLICATIONS

The International Searching Authoriy, International Search Report and Written Opinion issued for PCT/US2015/055693 dated Feb. 3, 2016, 12 pages, publisher EPO, Rijswijk.
(Continued)

*Primary Examiner* — Dwayne D Bost
*Assistant Examiner* — Stephen M Brinich

(57) ABSTRACT

A method includes obtaining data associated with an electronic component. The method also includes conducting a multi-tier inspection process to verify a conformance of the electronic component. Each of the tiers includes a different type of identification test, and at least one of the tiers is configured to provide fuzzy outputs. The method further includes analyzing the data associated with the electronic component using one or more first tests associated with a first of the tiers to determine whether the electronic component conforms to a pre-specified requirement. In addition, the method includes generating an output based on the analysis and determining whether additional testing is required using one or more next-level tests associated with another of the tiers.

23 Claims, 10 Drawing Sheets

(58) Field of Classification Search
CPC ..... G06T 7/001; G06T 7/0012; G06T 7/0014; G06T 7/0016
USPC .......................................... 382/141, 144–154
See application file for complete search history.

(56) References Cited

U.S. PATENT DOCUMENTS

| | | | | |
|---|---|---|---|---|
| 6,911,722 | B2* | 6/2005 | Ohuchi | H01L 21/563 257/684 |
| 7,177,458 | B1* | 2/2007 | Savareigo | G01N 21/956 250/559.45 |
| 2002/0028399 | A1* | 3/2002 | Nakasuji | G01N 23/225 430/30 |
| 2004/0086172 | A1* | 5/2004 | Guldi | H01J 37/3045 382/151 |
| 2006/0187719 | A1 | 8/2006 | Matsumoto et al. | |
| 2007/0223119 | A1 | 9/2007 | Takahashi | |
| 2008/0169831 | A1 | 7/2008 | Lu et al. | |
| 2009/0099830 | A1 | 4/2009 | Gross et al. | |
| 2010/0182421 | A1* | 7/2010 | Chidambaram | G01N 21/66 348/126 |
| 2010/0237854 | A1 | 9/2010 | Kumhyr et al. | |
| 2011/0220560 | A1 | 9/2011 | Verdegan et al. | |
| 2012/0124385 | A1 | 5/2012 | Klasen et al. | |
| 2012/0281908 | A1 | 11/2012 | Shirkhodaie et al. | |
| 2013/0022167 | A1 | 1/2013 | Cardoso et al. | |
| 2014/0077078 | A1* | 3/2014 | Hatakeyama | H01J 37/28 250/310 |
| 2015/0117701 | A1 | 4/2015 | Ross et al. | |
| 2016/0169818 | A1 | 6/2016 | Martin et al. | |

OTHER PUBLICATIONS

"TruView Hawk, Automated Optical Inspection", Creative Electron, Nov. 2014, 2 pages.

Griffin Lemaster, et al., "The Economics of Die Attach Voiding in LED Assemblies", Creative Electron, Inc., Jun. 2014, 5 pages, publisher Creative Electron, Inc., San Marcos, CA.

Dr. Bill Cardoso, et al., "WISE: Wavelet Image Spectra Enhancement of X-Ray Images", May 2014, 3 pages publisher Creative Electron, Inc., San Marcos, CA.

"10 ways to find counterfeit components using x-rays", Creative Electron, Nov. 2014, 15 pages, publisher Creative Electron, Inc., San Marcos, CA.

"Algorithms: The Next Frontier for X-Ray Inspection", Creative Electron, Nov. 2014, 18 pages, publisher Creative Electron, Inc., San Marcos, CA.

"ZVS-200S, Zyco Corporation's HVM in-tray inspection solution for FC-BGA", 2012, 2 pages, publisher Zygo Corporation, Quebec, Canada.

KLA TENCOR, ICOS CI-T120, Super High-Speed Component Inspection, 2009, 6 pages.

Notification of Transmittal of the International Search Report and the Written Opinion of the International Searching Authority dated Sep. 21, 2017 in connection with International Patent Application No. PCT/US2017/037705.

\* cited by examiner

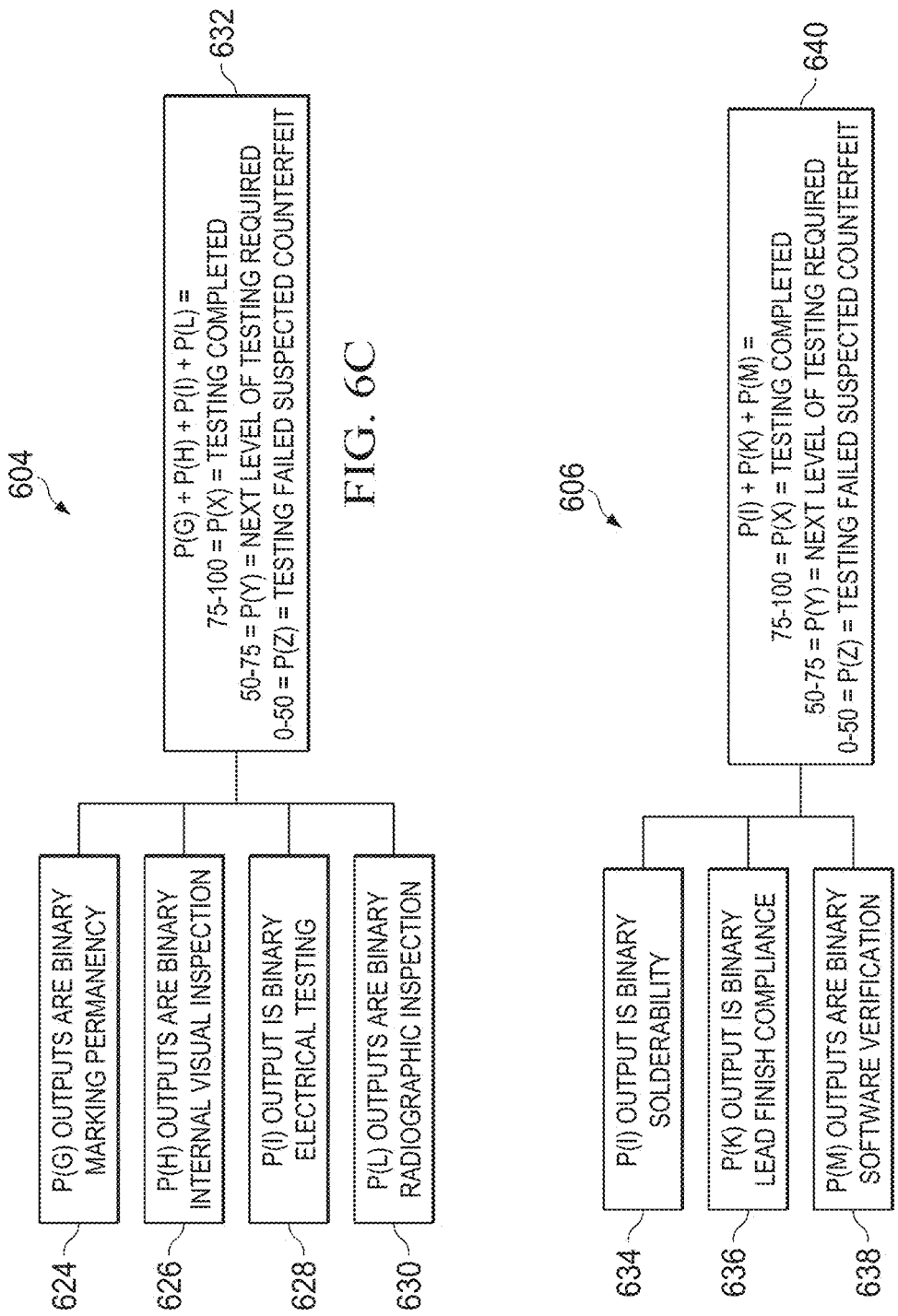

1100

| ESTIMATION IMPROVEMENT | | | |
|---|---|---|---|
| AVERAGE QUANTITY PARTS TESTED | 432 | | |
| CURRENT INSP METHOD | PROPOSED INSP METHOD | PHASE 2 PROPOSED INSP METHOD | |
| 7.84 | 3.92 | 1.96 | HOURS/PART |
| | | | |
| INCLUDES PART SEARCH/INSPECTION/DOCUMENTATION PER PART | | | |
| | 50% IMPROVEMENT | 75% IMPROVEMENT | |
| 3385.08 | 1692.54 | 846.27 | HOURS |
| $592,388.70 | $296,194.35 | $148,097.17 | |
| | $296,194.35 | $444,291.52 | ROI SAVINGS |

| ESTIMATION CURRENT ACCURACY | | |
|---|---|---|
| HOURS/ESTIMATED HOURS | | |
| | COMBINED | 61.40 HOURS UNDERESTIMATED |
| | | |
| PREDICTION ESTIMATION METHOD | | |
| THIS TECHNIQUE REPRESENTS 95% OF THE DATA WITHIN THE TOLERANCE RANGES | | |
| THE REMAINING 5% OF THE DATA ARE WITHIN 1-2 HOURS OF THE HIGHEST TOLERANCE RANGE | | |

FIG. 12

AUTOMATED MODEL-BASED INSPECTION SYSTEM FOR SCREENING ELECTRONIC COMPONENTS

TECHNICAL FIELD

This disclosure is generally directed to the detection of counterfeit articles. More specifically, this disclosure is directed to an automated model-based inspection system for screening electronic components.

BACKGROUND

A growing worldwide problem involves non-conforming components including counterfeit electronic components, such as counterfeit integrated circuit chips. For example, a counterfeiter may sand off the top surface of an integrated circuit chip, cover the chip with a new top surface, print new markings on the chip, and try to pass off the chip as a new or different type of chip. This process is commonly referred to as "blacktopping" since the new top surface placed on the integrated circuit chip is typically black. Also, non-conforming components include products with missing components, incorrect orientations of components, or technical data package (TDP) violations. The potential monetary losses associated with buying or selling counterfeit electronic components could easily reach into millions of dollars and impact product's reliability.

Conventional approaches for detecting non-conforming electronic components often fall into one of two categories. First, human inspectors compare components to a known "good" reference component. Unfortunately, these approaches are often limited to a single inspection technique and small sample sizes, are subject to human error, and require lengthy inspection times. Second, internal structures of the electronic components can be analyzed using various inspection techniques. For example, product inspections may look for damage or mechanical non-compliance. However, a manual research process is often required in order to determine testing/inspection requirements.

SUMMARY

This disclosure provides an automated model-based inspection system for screening electronic components.

In a first embodiment, a method includes obtaining data associated with an electronic component. The method also includes conducting a multi-tier inspection process to verify a conformance of the electronic component. Each of the tiers includes a different type of identification test and historical analysis, and at least one of the tiers is configured to provide fuzzy outputs. The method further includes analyzing the data associated with the electronic component using one or more first tests associated with a first of the tiers to determine whether the electronic component conforms to a pre-specified requirement. In addition, the method includes generating an output based on the analysis and determining whether additional testing is required using one or more next-level tests associated with another of the tiers.

In a second embodiment, an apparatus includes at least one memory configured to store data associated with an electronic component. The apparatus also includes at least one processing device configured to obtain the data associated with the electronic component and conduct a multi-tier inspection process to verify a conformance of the electronic component. Each of the tiers includes a different type of identification test and historical analysis, and at least one of the tiers is configured to provide fuzzy outputs. The at least one processing device is also configured to analyze the data associated with the electronic component and obtained via one or more first tests associated with a first of the tiers to determine whether the electronic component conforms to a pre-specified requirement. The at least one processing device is further configured to generate an output based on the analysis and determine whether additional testing is required using a process associated with another of the tiers.

In a third embodiment, a non-transitory computer readable medium contains instructions that, when executed by at least one processing device, cause the at least one processing device to obtain data associated with an electronic component and conduct a multi-tier inspection process to verify a conformance of the electronic component. Each of the tiers includes a different type of identification test and historical analysis, and at least one of the tiers is configured to provide fuzzy outputs. The medium also contains instructions that, when executed by the at least one processing device, cause the at least one processing device to analyze the data associated with the electronic component using one or more first tests associated with a first of the tiers to determine whether the electronic component conforms to a pre-specified requirement. The medium further contains instructions that, when executed by the at least one processing device, cause the at least one processing device to generate an output based on the analysis and determine whether additional testing is required using one or more next-level tests associated with another of the tiers.

In a fourth embodiment, a system includes handling equipment configured to position electronic components for inspection, imaging equipment configured to obtain data associated with each electronic component, and scanning equipment configured to move at least one of the imaging equipment and the electronic components so that the imaging equipment is able to obtain the data associated with each electronic component. The system also includes an analysis system configured to conduct a multi-tier inspection process to verify an authenticity of the electronic components. Each of the tiers includes a different type of identification test and historical analysis, and at least one of the tiers is configured to provide fuzzy outputs, and wherein at least one of the tiers is configured to provide fuzzy outputs. The analysis system is also configured to analyze the data associated with the electronic components using fuzzy logic to determine whether each of the electronic components is conforming.

Various implementations of these embodiments can provide various advantages depending on the implementation. For example, conventional inspection systems are often able to perform an analysis of inspected components using a single predefined algorithm or a predefined set of algorithms and lack the ability to flexibly select one or more algorithms to be applied based on the data received. The embodiments described here support the flexible selection of the algorithm(s) to be used to inspect electronic components. Among other things, this can allow multiple types of electronic components to be inspected using the inspection system. Moreover, the embodiments described here provide for faster inspections of electronic components and support repeatable processes that are not subject to human error. In addition, the embodiments described here can be used to inspect all or substantially all electronic components in a batch of products, which can help to increase confidence in the authenticity of the electronic components in the batch.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 6A through 6D illustrate an example conditional framework for automatic optical inspection to be used for screening electronic components according to this disclosure;

FIGS. 10 through 12 illustrate example analysis results associated with electronic components according to this disclosure.

DETAILED DESCRIPTION

FIGS. 1 through 13, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

Embodiments of the present disclosure provide for a system and method for automated model-based inspection system for screening electronic components to detect counterfeit articles. Anti-counterfeit package labeling includes: Quick response (QR) codes, which could be scanned for validation; Print features such as print markings on the packaging; Cold foling such as silver foil applied to package; Void material, namely, wording of VOID can appear to ensure package has not been tampered with; RFID tags, which may be hidden under labels depending on requirements; Thermochromatic ink, in which exposure to heat will make print features appear or disappear; a two-dimensional (2D) matrix/barcode, such as encoded text or images from arranged "square"; Microtext, which is smaller printed text that cannot be seen by the human eye; and Holograms/fluorescent inks.

Figure 1:
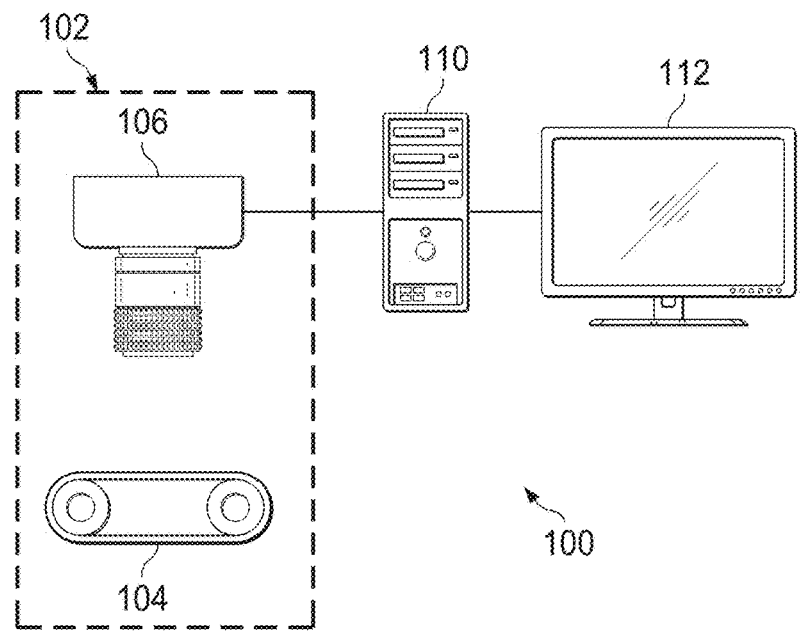
FIG. 1 illustrates an example automated model-based inspection system for screening electronic components to detect counterfeit articles according to this disclosure.

FIG. 1 illustrates an example automated model-based inspection system 100 for screening electronic components to detect counterfeit articles according to this disclosure. The embodiment of the system 100 shown in FIG. 1 is for illustration only. Other embodiments could be used without departing from the scope of the present disclosure.

In the example shown in FIG. 1, an inspection station 102 includes an inspection platform 104 and an imaging system 106. The inspection station 102 screens various articles for non-conforming articles, such as non-standard components and counterfeited articles like fraudulently-copied or imitation components and counterfeit integrated circuit chips. Non-conforming components can include non-standard articles manufactured by an approved manufacturer but that fail to meet specifications detailed in a plan drawing or design, that contain missing components, incorrect orientation of components, and the like, or that have technical data package (TDP) violations.

The inspection platform 104 includes any suitable structure for carrying, holding, or presenting one or more of a number and variety of products for inspection. For example, the inspection platform 104 could include a table or support surface configured to support a tray, a tape and reel, a sealed blister pack or another package, a planar printed wire board (PWB), or a surface of a three dimensional hybrid PWB assembly. The interface platform 104 could also include a suitable surface for holding and presenting a product for inspection by one or more cameras of the imaging system 106.

The imaging system 106 denotes a vision system that can capture images and extract application-specific information from the captured images. The imaging system 106 could also generate event descriptions or make decisions that are used in an intelligent and automated system. The imaging system 106 includes at least one camera, such as a smart camera or intelligent camera. Each camera denotes a visual image capture system, such as an array of lenses, image sensors, and one or more processors, an image memory, and programmable and data memory configured to store data and instructions for use by the one or more processors. The imaging system 106 can be a self-contained, standalone vision system with at least one built-in image sensor. The imaging system 106 also includes one or more communication interfaces, such as an Ethernet interface, a wireless transceiver, an optical interface, or an industry-proof 24V I/O line for connection to a programmable logic controller, actuator, relay, or pneumatic valve.

The inspection station 102 is coupled to an analysis system 110. While shown here as being separate, the analysis system 110 could be included in the inspection station 102. The analysis system 110 is configured to receive outputs from the imaging system 106, such as captured data, application-specific information, and other image information. In some embodiments, the analysis system 110 controls one or more aspects of the imaging system 106, the inspection platform 104, or both.

The analysis system 110 analyzes the data from the inspection station 102 to identify non-standard components. The analysis system 110 outputs binary, numeric, and fuzzy logic numbers, i.e., fuzzy outputs. For example, the analysis system 110 could perform the following tasks at each inspection stage:

automatically identify a part or assembly;

automatically retrieve technical data reference information needed for optical comparison of that part or assembly;

automatically perform optical inspection and comparison of dimensions and required portions of the part or assembly, which helps to ensure that the part or assembly is fully compliant;

automatically inspect and compare workmanship and industry standards to help identify counterfeit components, such as (but not limited to) via Institute of Printed Circuits (IPC), or Military and commercial specifications (as required);

automatically compare historical and database data of the supplier, vendor, or manufacturer; and automatically decide how to handle the part or assembly, such as by determining whether to send the part or assembly for rework, engineering evaluation, return to vendor, or an assembly process.

In this document, the terms "automatic" and "automatically" refer to actions taken by an analysis system in response to other actions and without user intervention. In some embodiments, the analysis system 110 automatically verifies a quality and workmanship of critical aspects of a product, such as a connection or solder joint. The analysis system 110 could also provide an aid for human inspectors to perform a faster and more efficient inspection operation, increasing throughout and yields. The analysis system 110 can include automated instructions, via projections on parts, text or others, for the human to reference as to what to inspect. The analysis system 110 includes one or more processors and one or more storage devices configured to store data and instructions for use by the one or more processors. A memory and a persistent storage are examples of storage devices, which represent any structure(s) capable of storing and facilitating retrieval of information (such as data, program code, and/or other suitable information on a temporary or permanent basis). The memory can represent a random access memory or any other suitable volatile or non-volatile storage device(s). The persistent storage can contain one or more components or devices supporting longer-term storage of data, such as a read only memory, hard drive, flash memory, or optical disc. As described in more detail below, the analysis system 110 can use a combination of logic techniques, such as traditional fuzzy logic and an artificial neural network (ANN), for inspection and decision making.

In some embodiments, the analysis system 110 is coupled to or includes a display interface 112. The display interface 112 can denote any suitable display device, such as a liquid crystal display, touch screen display, or other display capable of rendering text and/or at least limited graphics, such as from web sites.

The system 100 is capable of performing multiple inspection tasks for numerous types of inspections, from initial inspection to final inspection, and is capable of automatically identifying non-conformances quickly. As opposed to simply comparing an image to a database of known "good" images, the system 100 can use a combination of comparison-based, fuzzy logic, and artificial intelligence techniques to make decisions on a case-by-case basis. The combination of these techniques enables the system 100 to inspect various assemblies or parts without a manually-entered database of images for comparison. The system 100 not only gathers data from images but can also connect with other databases to gather part features and requirements.

In some embodiments, prior to ANN utilization, an image captured by the imaging system 106 can be pre-processed to remove artifacts and background features that might otherwise complicate and increase the computational power required for the next steps in the analysis. Once the excess features are removed, the system 100 can attempt to measure features and look for non-conformities based on a comparative analysis with known good and bad images stored in a database. If the system 100 does not detect any images for comparison, the ANN in the analysis system 110 can determine the compliance of the part or assembly. This logic flow allows the part to be accurately inspected without excess computational requirements, which correlate to process time.

Figure 2:
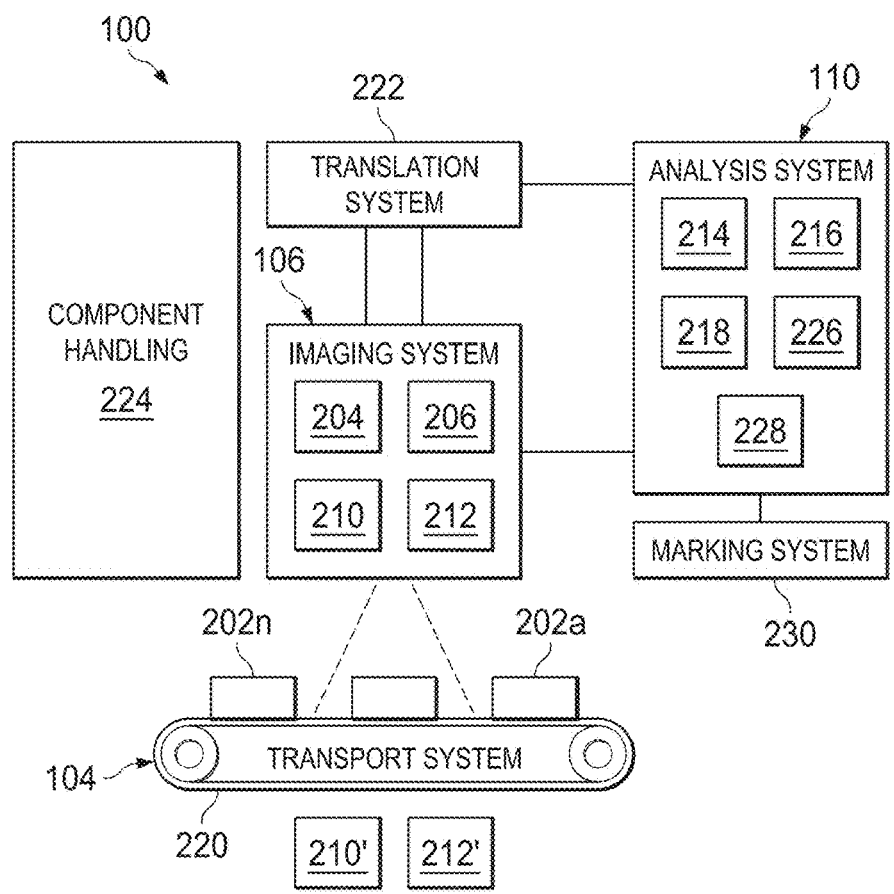
FIG. 2 illustrates additional details of an example automated model-based inspection system for screening electronic components to detect counterfeit articles according to this disclosure.

FIG. 2 illustrates additional details of an example automated model-based inspection system 100 for screening electronic components to detect counterfeit articles according to this disclosure. In this example, the system 100 is used to inspect various electronic components 202a-202n and determine whether the electronic components 202a-202n are potentially non-conforming. The electronic components 202a-202n can denote any suitable components to be inspected, such as integrated circuit chips, other circuit components (such as resistors, capacitors, inductors, diodes, and so forth), or integrated circuit chips or other circuit components mounted on structures. The components 202a-202n may be packaged in any of numerous ways that such components are delivered to end users. For example, the electronic components 202a-202n could be provided on a tray, in a tape and reel, sealed in blister packs or other packages, mounted on either side of a planar PWB, or mounted on any surface of a three dimensional hybrid PWB assembly. In general, any components that could be used in electronic devices or systems and that have one or more features capable of being used to distinguish between authentic and non-conforming articles can be inspected by the system 100. Note that the electronic components 202a-202n in FIG. 2 could represent individual components or collections of components.

As shown in FIG. 2, the system 100 includes the imaging system 106, which collects data regarding the electronic components 202a-202n being inspected. For example, the imaging system 106 could capture visual images, infrared images, X-ray wavelength data, mass spectrometry and/or spectroscopic measurements of the electronic components 202a-202n. Any other or additional data could be collected by the imaging system 106. In some embodiments, when more than one imaging technique is utilized, the corresponding data sets can be overlayed and consolidated to create a combined multi-spectral dataset.

The imaging system 106 includes any suitable structure for capturing information about the appearance, structure, or composition of electronic components being inspected. In some embodiments, the imaging system 106 includes a smart camera configured to capture visual images or perform vision acquisition or scanning The imaging system 106 here includes one or more processors 204 and one or more storage devices 206. The imaging system 106 here also includes at least one radiation source 210 and at least one radiation detector 212. As shown in FIG. 2, each radiation source 210 generates some form of radiation that is directed toward the electronic components 202a-202n. Example radiation sources 210 include visible, infrared, and ultraviolet light sources (such as light emitting diodes) and X-ray sources. A radiation source 210 may also be mounted at another location, such as below the electronic components 202a-202n and/or inspection platform 104 at location 210'. Each radiation detector 212 detects radiation that has interacted with or that is generated by the electronic components 202a-202n. Example radiation detectors 212 include digital cameras, infrared detectors (including near, short-wave, or long-wave detectors), X-ray sensors, and X-ray fluorescence (XRF) spectrometers. A radiation detector 212 may also be mounted at another location, such as below the electronic components 202a-202n and/or inspection platform 104 at location 212'. In some embodiments, at least one radiation source 210 represents a homogenous and polarization-insensitive source that generates white light. Also, in some embodiments, at least one radiation detector 212 represents a high-magnification telecentric optical system.

In particular embodiments, one type of radiation could be directed at the electronic components 202a-202n, or multiple types of radiation could be directed at the electronic components 202a-202n. The type(s) of radiation could be selected based on various factors, such as the type of electronic component being inspected. Also, different types of radiation could be used at different times. For example, optical inspections could be performed for all electronic components 202a-202n using visible light, and X-ray or XRF inspections could be performed only for electronic components 202a-202n of questionable authenticity.

Any suitable image(s) of an electronic component can be captured by the imaging system 106. For example, the imaging system 106 could capture instantaneous one-dimensional line scans, produce two-dimensional (2D) images, produce representations of three-dimensional (3D) surface features, or any combination thereof. Moreover, the imaging system 106 could generate data in any suitable manner, such as by combinations, comparisons, or mixing of wavelength-dispersed data, polarization data, or other optical or electronic representations of information associated with the optical physics contributing to an image (including results in transformational or reciprocal spaces, like Fourier or wavelet transforms). Additionally, digital filters (including digital filters matched to data characteristics requiring discrimination and analysis) could be used in the imaging system 106.

The data collected by the imaging system 106 is provided to the analysis system 110, which analyzes the data to determine whether the electronic components 202a-202n are potentially non-conforming. The analysis system 110 includes any suitable computing or processing system configured to analyze data associated with electronic components being inspected and determine whether the electronic components may be counterfeit. In this example, the analysis system 110 includes at least one processing device 214, at least one memory 216, and at least one communication interface 218. Each processing device 214 includes any suitable processing or computing device(s) configured to process information, such as a microprocessor, microcontroller, digital signal processor, field programmable gate array, application-specific integrated circuit, or other device(s). Each memory 216 includes any suitable storage and retrieval device(s), such as a volatile and/or non-volatile memory. Each communication interface 218 includes any suitable interface(s) configured to transmit or receive data, such as an Ethernet network interface or a radio frequency (RF) transceiver.

The inspection platform 104 can include or be associated with a transport system 220. The transport system 220 moves the electronic components 202a-202n into a suitable position for imaging by the imaging system 106. The transport system 220 includes any suitable structure for moving electronic components into an imaging position. Example types of transport systems 220 include one or more conveyor belts, tape and reel devices, movable trays, or robot pick and place devices. The type of transport system 220 used could vary depending on certain factors, such as whether the electronic components 202a-202n denote loose integrated circuit chips or printed circuit boards with connected integrated circuit chips.

The system 100 can also or alternatively include a translation system 222 that moves the imaging system 106 into a suitable position to measure one or more electronic components 202a-202n. For example, a large number of electronic components 202a-202n could be held in a tray. The translation system 222 could move the imaging system 106, responsive to control signals from the analysis system 110, along rows and columns of electronic components to allow scanning of the electronic components. The translation system 222 includes any suitable structure for moving an imaging system in order to image electronic components. One example type of translation system 222 is a gantry XYZ system.

Component handling equipment 224 can be provided to facilitate proper placement and positioning of the electronic components 202a-202n, such as on the transport system 220 or near the imaging system 106. For example, the component handling equipment 224 could include equipment for moving, correctly orienting, and positioning the electronic components 202a-202n being screened so that data about the electronic components 202a-202n can be collected correctly. Any suitable component handling equipment 224 could be used here, such as robotic equipment.

Non-conforming electronic components routinely include one or more detectable attributes. For example, integrated circuit chips routinely include markings such as manufacturer logos, part numbers, date codes, lot codes, and "pin 1" dimple marks on tops or bottoms of the chips. Differences in date or lot codes, fonts, letter sizes, letter spacings, or logos can be indicative of counterfeit items. Also, markings may be laser etched into authentic products and printed (such as via ink jet printers) onto counterfeit products, so differences in spectral reflectivity or "splotchiness" of markings can be indicative of counterfeit items. Further, spatial displacement of logos or other markings can be indicative of counterfeit items. Other attributes that may be indicative of counterfeiting include the finish, reflectivity, and flatness (or irregularity in flatness) of the top surfaces of integrated circuit chips, the dimensions of the overall chips, the height of molded portions of the chips, and the edge straightness of molded portions of the chips. Still, other attributes that may be indicative of counterfeiting include the count, style, geometry, symmetry, and flatness of solder leads. Component location, size, or orientation may also be indicative of a non-conforming part. In addition, varied part or component numbers, numbers of components, or other differences against a design plan can be indicative of a non-conforming part.

Any of these or other features (or any combination thereof) can be analyzed by the analysis system 110 in order to detect potentially non-conforming products. In FIGS. 1 and 2, the analysis system 110 supports various analysis algorithms that can be stored in the at least one memory 216 and executed by the at least one processing device 214. Each analysis algorithm could define both (i) the types of data to be analyzed by the system 100 and/or the manner in which the data is to be collected by the system 100 and (ii) the analysis routine(s) to be applied to the data collected by the system 100. The algorithms can be optimized to detect various attributes that are indicative of potential counterfeiting. The optimizations can include, for instance, those for maximum throughput, highest accuracy, highest or lowest false accept rate, or other processing criteria.

In some embodiments, the analysis system 110 includes an ANN 226 and a fuzzy logic unit 228. The ANN 226 operates in conjunction with the fuzzy logic unit 228 to perform an automated optic inspection (AOI) process. The ANN 226, augmented by the fuzzy logic unit 228, is able to improve efficiency of product/component inspections. For example, the ANN 226 can use the fuzzy logic unit 228 to learn additional aspects or elements in order to improve the inspection process. As a particular example, the ANN 226 and the fuzzy logic unit 228 can create additional algorithms stored in the at least one memory 216 to conduct the inspection process. The fuzzy logic 228 analyzes analog input values in terms of logical variables that take on continuous values between 0 and 1, in contrast to classical or digital logic, which operates on discrete values of either 1 or 0. That is, the fuzzy logic 228 outputs fuzzy outputs that are based in degrees of values between 0 and 1 instead of just pass or fail. The fuzzy outputs, as degrees of possible failure or pass enable the ANN 226 to improve a probability and efficiency in identifying non-conforming components.

In some embodiments, the ANN 226 is capable of pattern recognition. For example, the ANN 226 can analyze image information captured by the imaging system 106. The ANN 226 could detect words, characters, symbols, sizes, shapes, spatial orientations, spatial distances, component proximities and orientations, and numerical inputs. The ANN 226 can receive one or more inputs, such as numerical inputs, via one or more external systems, one or more internal databases (such as stored in the at least one memory 216), one or more external databases, or the display interface 112 (shown in FIG. 1). In some embodiments, the ANN 226 utilizes a percent accuracy threshold and a probability matrix to determine whether a product/component is conforming or non-conforming.

The fuzzy logic unit 228 determines output based on multiple inputs received, or input, from different databases, rejected values, approved values, and different probabilities. The different databases can be from external sources, such as different design systems that include a design specification for the product/component. The fuzzy logic unit 228 enables the ANN 226 to learn using previous determinations as inputs. The previous determinations can include "yes" or "no," "good" or "bad," false positives, and so forth.

The analysis system 110, through the ANN 226 and the fuzzy logic unit 228, analyzes image information captured by the imaging system 106. The analysis system 110 performs pattern recognition on the captured images to identify non-conforming components. For example, when visual images are provided, the ANN 226 and the fuzzy logic unit 228 select or develop algorithms to detect spatial characteristics, such as quantity, dimensions, and spatial orientations and proximities to other components. The ANN 226 and the fuzzy logic unit 228 also select or develop algorithms to detect evidence of re-marking, blacktopping, or other tampering with the electronic components 202a-202n. When X-ray scans are provided, the ANN 226 and the fuzzy logic unit 228 select or develop algorithms to detect and verify the internal construction of the electronic components 202a-202n. When XRF spectrographic measurements are provided, the ANN 226 and the fuzzy logic unit 228 select or develop algorithms to detect and verify the elemental constituents of the electronic components 202a-202n. The ANN 226 and the fuzzy logic unit 228 could also vary their inspections based on the electronic components 202a-202n being inspected.

In some embodiments, the analysis system 110 supports a three-tier approach to inspecting the electronic components 202a-202n, and the analysis system 110 could apply different weights to each of the three tiers. In each tier, the analysis system 110 can estimate an amount of time required to conduct an inspection in the respective tier. The estimate by the analysis system 110 can be provided to the display interface 112 to be displayed and provide an operator with an estimate to assist planning operations. In some embodiments, the estimate can also be used prior to AOI testing and inspection to help job scheduling. In each of the subsequent tiers, the analysis system 110 could conduct a more thorough inspection than was performed in a previous tier. For instance, in the first tier, an initial inspection can be performed. If the analysis system 110 detects a non-conforming product/component, the analysis system 110 ceases the inspection process and informs the operator via the display interface 112. If the analysis system 110 does not detect a non-conforming product/component, the analysis system 110 can proceed to a second tier for further analysis. In the second tier, the analysis system 110 uses additional algorithm(s) and an increased variance weight to identify more minute non-conformities. In the second tier, the analysis system 110 can cause the imaging system 106 to capture additional visual, thermographic, spectral, or X-ray images of the product/component. If the analysis system 110 detects a non-conforming product/component in the second tier, the analysis system 110 ceases the inspection process and informs the operator via the display interface 112 for further human inspection. If the analysis system 110 does not detect a non-conforming product/component in the second tier, the analysis system 110 can proceed to a third tier for further analysis. In the third tier, to identify even more minute non-conformities, the analysis system 110 uses additional algorithm(s) and an increased variance weight over that used in the second tier. In the third tier, the analysis system 110 can cause the imaging system 106 to capture additional visual, thermographic, spectral, or X-ray images of the product/component. If the analysis system 110 detects a non-conforming product/component in the third tier, the analysis system 110 ceases the inspection process and informs the operator via the display interface 112 for further human inspection. If the analysis system 110 does not detect a non-conforming product/component in the third tier, the analysis system 110 provides the product/component as "passed" or for further processing.

The analysis algorithms selected or developed by the ANN 226 and the fuzzy logic unit 228 and executed by the analysis system 110 could vary based on any other factors. Other factors could include the positioning accuracy requirements of the electronic components 202a-202n, the image capture speed or field of view of an imaging device used to image the electronic components 202a-202n, and the packaging of the electronic components 202a-202n (or lack thereof). For instance, the ANN 226 and the fuzzy logic unit 228 may employ different algorithms depending on whether integrated circuit chips are loose or soldered to printed circuit boards.

In some embodiments, the ANN 226 and the fuzzy logic unit 228 are able to detect non-conforming electronic components with or without reference to a "golden" or "reference" component (a known good/authentic component). Known good dies or references can change periodically with updated rev's of parts or components. The golden or reference components are interchangeable depending on updated specifications from vendors/suppliers. For example, once the type of electronic component being inspected is identified, the fuzzy logic unit 228 causes the ANN 226 to access a database of records to identify one or more expected characteristics of that type of electronic component. The expected characteristics could be based on one or more characteristics of at least one known good component, historical data associated with multiple lots of known good components, or any other suitable data. Differences between the measured characteristic(s) of the electronic components 202a-202n and the expected characteristic(s) could be indicative of counterfeiting. The ANN 226, with the fuzzy logic unit 228, could learn to also or alternatively measure and compare one or more characteristics of the electronic components 202a-202n themselves, such as to identify the variability of the characteristic(s) within a single lot of the electronic components 202a-202n. Excessive variations in the measured characteristic(s) of the electronic components 202a-202n could again be indicative of non-conforming components.

In this way, the system 100 can be used to provide rapid throughput for the screening of all or substantially all components in a lot, which can be accomplished with little or no human intervention in the inspection process. The system 100 also enables non-destructive screening for specific counterfeit methods that are traditionally only found through destructive screening methods. Inspections can be conducted per appropriate industry standards for non-conforming parts, and multiple analyses (even those involving different spectrums of radiation) could be performed for each individual electronic component at the same time. Algorithms can be developed and customized to detect evidence of specific counterfeiting techniques or specific non-conforming tendencies, and the fuzzy logic unit 228 can cause algorithms to be automatically created, updated, or introduced during processing to deal with variations, changes, or improvements in counterfeiting techniques. In addition, the system 100 can detect non-conforming electronic components more rapidly, which enables the testing of every single electronic component for non-conformance (rather than a very small subset of the electronic components). Additional details regarding example implementations and operations of the system 100 are provided below.

Note that each algorithm here can be implemented in any suitable manner, such as via computational or physical mechanisms. For instance, an algorithm could be implemented via software/firmware instructions or via hardware logic. Also, the automatic creation or selection of algorithms can involve the selection of a computational algorithm and/or the selection of hardware, physical operations, subsequent flexible algorithmic processing, and pass/fail determinations. For example, based on an irregularity in font shape, the ANN 226 might select a process to perform an inspection for leadwire bonding irregularities.

In addition, note that the system 100 described here could find use in a number of environments. For example, the system 100 could be used as part of a "final gate" component acceptance process at electronic assembly houses, brokers, distributors, and test houses. Specific industries where this functionality might be particularly useful include the defense industry (where counterfeit products raise reliability concerns of military hardware) and the medical and energy industries (where counterfeit products raise significant concerns for liability or patient harm).

To support the identification of electronic components 202a-202n that are determined to be potentially non-conforming, a marking system 230 can be provided in the system 100. The marking system 230 could be used to create a visible or other marking on an electronic component determined to be potentially counterfeit. Any suitable mechanism can be used to create a visible or other marking on an electronic component.

Although FIGS. 1 and 2 illustrate one example of an automated model-based inspection system 100 for screening electronic components to detect counterfeit articles and related details, various changes may be made to FIGS. 1 and 2. For example, various components in FIGS. 1 and 2 could be combined, subdivided, rearranged, or omitted or additional components could be added according to particular needs. As a specific example, the functionality of the imaging system 106 and the analysis system 110 could be combined.

Figure 3:
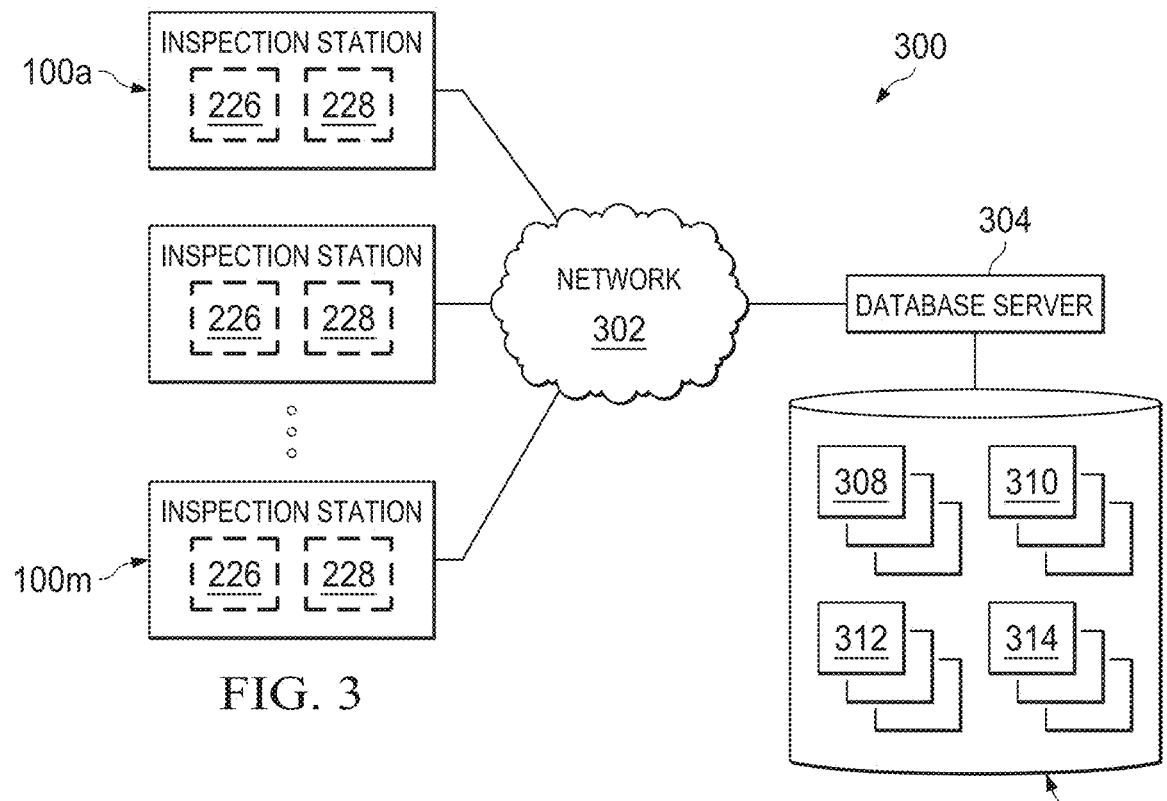
FIG. 3 illustrates an example distributed system for screening electronic components to detect counterfeit articles according to this disclosure.

FIG. 3 illustrates an example distributed system 300 for screening electronic components to detect counterfeit articles according to this disclosure. As shown in FIG. 3, the system 300 includes multiple automated model-based inspection systems 100a-100m, each of which could be the same as or similar to the system 100 shown in FIGS. 1 and 2 and described above. The systems 100a-100m here could be used at a single location or at multiple locations (and possibly separated by large distances).

The system 300 also includes a network 302. The network 302 may include wired communication links, wireless communications links, or a combination of wired and wireless communications links. The network 302 facilitates communication between various components coupled to the network 302. For example, the network 302 may communicate Internet Protocol (IP) packets, frame relay frames, Asynchronous Transfer Mode (ATM) cells, or other suitable information between network addresses. The network 302 may include one or more local area networks, metropolitan area networks, wide area networks, all or a portion of a global network, or any other communication system(s) at one or more locations.

One or more database servers 304 are coupled to the network 302 and control access to and use of one or more databases 306, which store various information used by the systems 100a-100m. For example, the database 306 could store data records 308 identifying the characteristics of different "golden" or reference electronic components. These characteristics define the expected characteristics of electronic components and can be compared to measured characteristics of electronic components 202a-202n to identify potential counterfeiting. The characteristics in the data records 308 could be identified in any suitable manner, such as by testing known good lots of electronic components or by obtaining information about manufacturing capabilities or tolerance thresholds of electronic component manufacturers.

The database 306 could also store data records 310 identifying permissible product-to-product variations within a single lot of electronic components. If components in a single lot exhibit variations above the permissible levels, this can be used to identify potential counterfeiting. Again, the information in the data records 310 could be obtained in any suitable manner, such as by testing known good lots of electronic components, by using information about manufacturing capabilities or tolerance thresholds of electronic component manufacturers, or by testing lots of unknown-quality components for variations of key characteristics within the lot.

The database 306 could further store algorithms 312, which can be distributed to the systems 100a-100m as the algorithms used or developed by the ANN 226 and the fuzzy logic unit 228. A system 100a-100m could request one or more algorithms 312 during startup, in response to identifying a particular type of electronic component being tested, at specified intervals, or in any other suitable manner. Among other things, this allows updated or new algorithms 312 to be easily provided to the systems 100a-100m. The database 306, independently or in coordination with other computing assets attached to the network 302, can provide guidance or updates to the fuzzy logic unit 228 in each system 100a-100n that guide the ANN 226 in the selection of development of algorithms to be applied to items undergoing inspection. In addition, the database 306 could store historical inspection data records 314, which include previous determinations and identify the results of various scans of electronic components.

The use of one or more central databases 306 could provide various benefits depending on the implementation. For example, information from multiple systems 100a-100m could be collected by the database server 304 and distilled for storage in the database 306. This information could include the results of inspections for numerous electronic components, and the inspection data could be sorted and used to perform various tasks. One task could include updating the data records 308-310 to reflect improved measurements of characteristics of known good products or improved measurements of variability in known good product lots. This can help to provide an intelligent update or learning feature for the inspection stations.

In some embodiments, the database(s) 306 can act as a single point of reference for all inspection stations. The database(s) 306 can also serve as an ever-evolving tool that sorts and files authentic versus counterfeit historic inspection data, provides a catalog for manually troubleshooting questionable parts, and provides a catalog of "golden standard" references of inspection values or variation in values for each component or component feature.

Although FIG. 3 illustrates one example of a distributed system 300 for screening electronic components to detect counterfeit articles, various changes may be made to FIG. 3. For example, the system 300 could include any number of inspection stations, networks, servers, and databases. Also, an inspection station could be configured to operate in a stand-alone manner without reference to the contents of one or more centralized databases 306.

Figure 4:
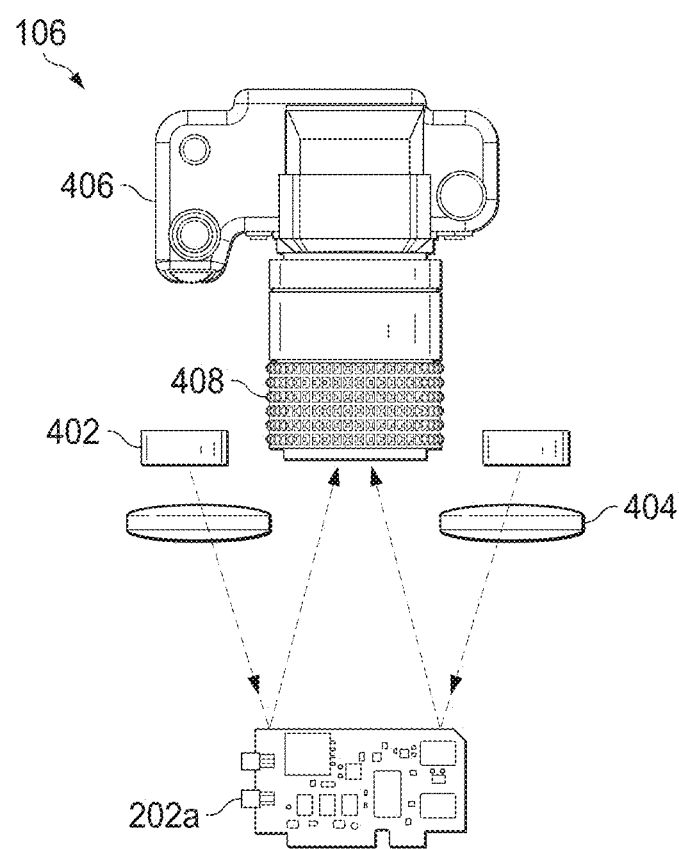
FIGS. 4 and 5 illustrate example electronic component scanning mechanisms for an inspection station according to this disclosure.
Figure 5:
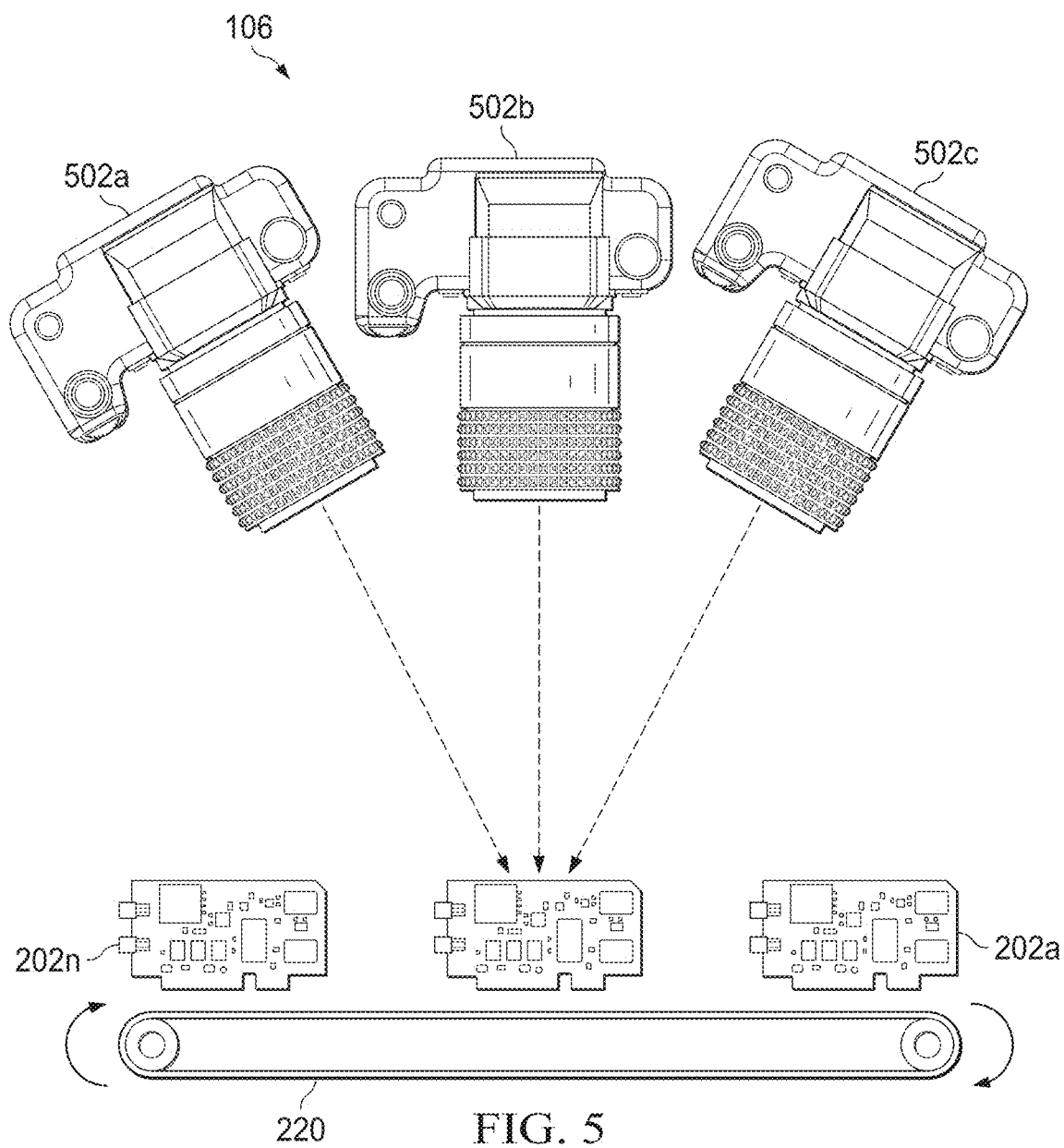

FIGS. 4 and 5 illustrate example electronic component scanning mechanisms for an inspection station according to this disclosure. More specifically, FIGS. 4 and 5 illustrate example implementations of the imaging system 106 in the system 100 of FIGS. 1 and 2. As shown in FIG. 4, one implementation of the imaging system 106 uses a ring light 402, which denotes one or more illumination devices (such as one or more light emitting diodes) arranged in a circular pattern or other pattern to illuminate an electronic component 202a from multiple directions. At least one linear polarizer 404 polarizes the generated light. Light reflecting off the electronic component 202a is captured using an imager 406, such as a smart digital camera, which includes a lens system 408 for focusing the light. Although not shown, the imager 406 may include another linear polarizer, which could be at a 90° orientation with respect to the polarizer 404, to help improve the image fidelity (brightness and contrast) of images captured by the imaging system 106.

In some embodiments, the ring light 402 represents a bright-field illuminator that generates white light. The size, location, angulation of beam axis, and divergence of the ring light 402 may be known, which helps during image processing. Bright-field illumination can be used to generate evenly illuminated, high brightness, high contrast images. Also, in some embodiments, the imager 406 represents a telecentric finite conjugate machine vision imaging optic, such as a high-magnification telecentric digital microscope, that automatically takes high fidelity photographs of all electronic components in a lot under inspection. The use of a telecentric imaging optic can help to maintain constant magnification and image size regardless of the depth of a focused feature, reducing errors caused by potential defocus. The imager 406 can have a certain degree of magnification combined with a high-resolution focal plane array (FPA) detector for high-fidelity imaging. The frame rate of the imager 406 can be fast enough to capture one or more images of every component being inspected, where the needed speed of the imager 406 is based (at least in part) on the speed of the transport system 220 and/or the translation system 222 and the desired inspection time.

Note that FIG. 4 illustrates the use of a single imager 406 to capture information about an electronic component being inspected. As shown in FIG. 5, multiple imagers 502a-502c could also be used to capture information about an electronic component being inspected. Illumination sources are omitted here for clarity. The imagers 502a-502c could represent visible-light cameras that capture images of the electronic component being inspected from multiple angles. The imagers 502a-502c could also denote different types of detectors (such as visible, infrared, X-ray, or spectroscopic detectors) that support different types of analyses. Any combination of imagers could be used in the imaging system 106. In the example shown in FIG. 5, the transport system 220 is implemented using a conveyor belt. This is for illustration only, and any other suitable type(s) of transport system(s) could be used to move electronic components. Additionally, the components 202a-202n in FIGS. 4 and 5 can represent a plurality of components, such as trays of integrated circuits, that are imaged substantially simultaneously, such as by using a single imager or imager array.

Although FIGS. 4 and 5 illustrate examples of electronic component scanning mechanisms for an inspection station, various changes may be made to FIGS. 4 and 5. For example, an inspection station could include any suitable detector(s) in any suitable arrangement(s) for capturing information about one or more electronic components under inspection.

FIGS. 6A through 6D illustrate an example conditional framework 600 for automatic optical inspection to be used for screening electronic components according to this disclosure. The conditional framework 600 could, for example, be implemented by the ANN 226 and the fuzzy logic unit 228 in the analysis system 110 to generate, select, and execute the appropriate algorithm(s) for analyzing data about one or more electronic components 202a-202n being inspected.

Figure 6A:
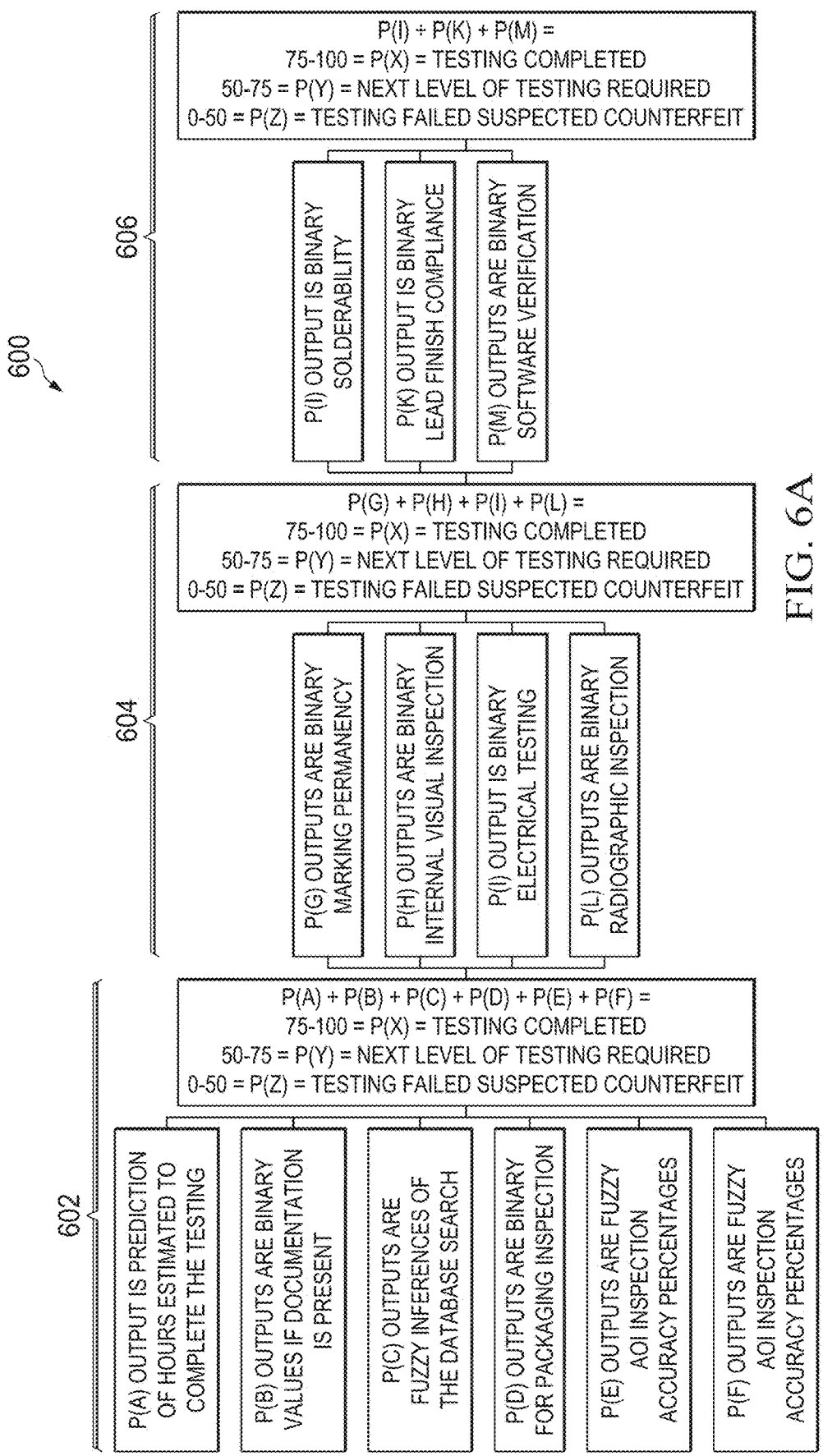

As shown in FIG. 6A, the flexible conditional framework 600 includes a "tier one" algorithm 602, a "tier two" algorithm 604, and a "tier three" algorithm 606. The "tier one" algorithm 602 performs an initial analysis of data associated with an electronic component 202a-202n and determines whether further testing, such as via the "tier two" algorithm 604, will be used during the inspection of that electronic component 202a-202n. The "tier two" algorithm 604 performs additional analysis of data associated with the electronic component 202a-202n and determines whether further testing, such as via the "tier three" algorithm 606, will be used during the inspection of that electronic component 202a-202n.

Figure 6B:
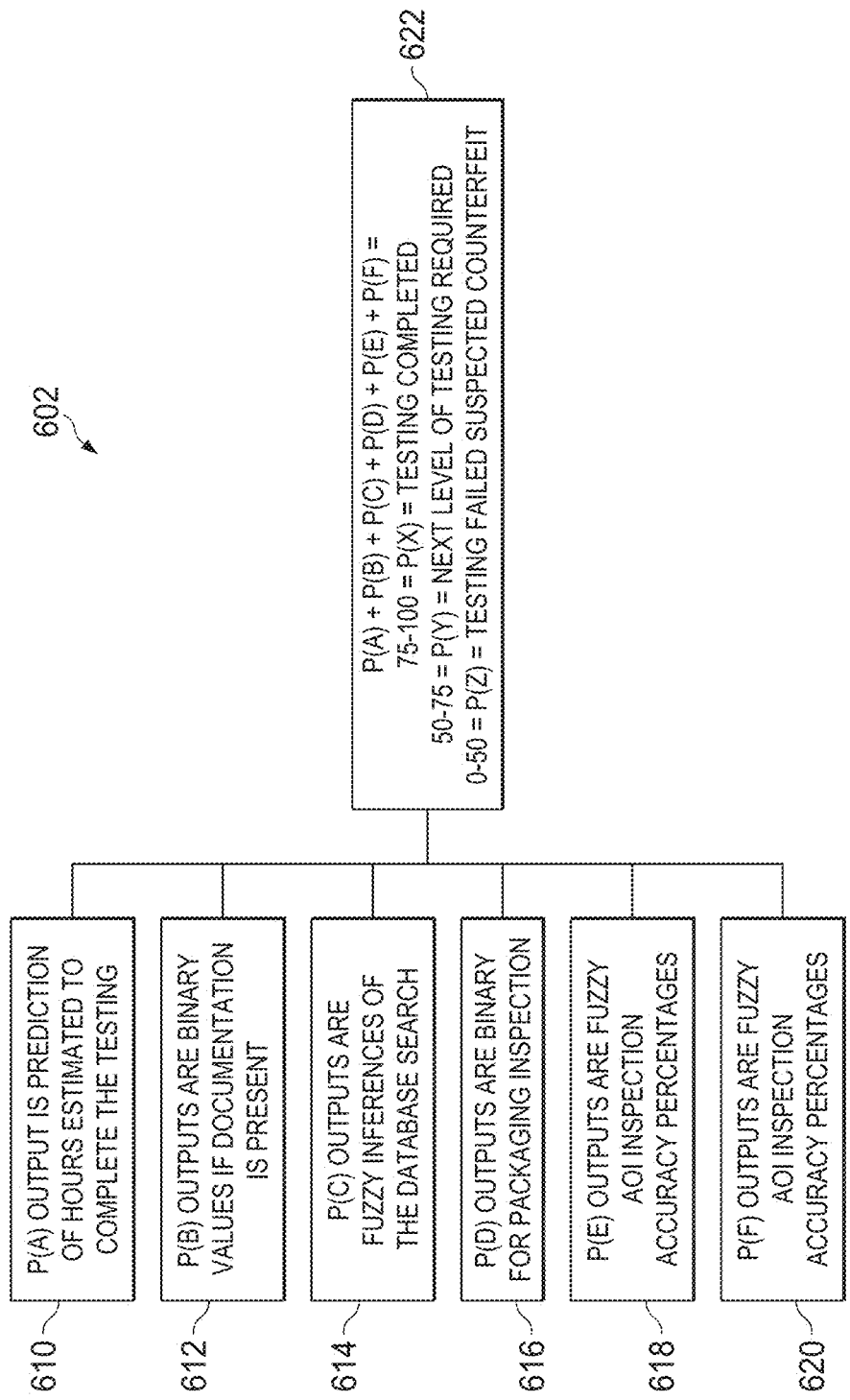

As an example, the "tier one" algorithm 602 can operate in response to a first set of defined condition logic. As shown in FIG. 6B, the analysis system 110 may receive a number of user inputs "P(A)". The user inputs can include a type of component being tested, a number of potential components being inspected, a part number of the component being tested, and a manufacturer of the components. In block 610, the ANN 226 determines and outputs a prediction of hours estimated to complete the testing. The analysis system 110 may also conduct a documentation review "P(B)" to determine if documentation exists for the respective inspection and/or electronic component 202a-202n. The document review, P(B), can include manufacturer logo identification information, document alternations, and barcode information. If documentation is present for P(B), the ANN 226 outputs binary values in block 612.

The analysis system 110 may further conduct a database search "P(C)". The searched databases can include a number of different databases, such as Government-Industry Data Exchange Program (GIDEP), Office of Personnel Management (OPM), Cleaning Industry Management Standards (CIMS), HIS, QT Meta Language (QML)/Qualified Products List (QPL), trusted foundry, and prior testing databases. The ANN 226, using the fuzzy logic unit 228, outputs fuzzy inferences of the database search in block 614.

The analysis system 110 may conduct AOI including optical component inspection by performing P(D) packaging inspection, P(E) external visual inspection, and P(F) dimensional inspection. In block 616, the ANN 226 outputs binary values for packing inspection. The packaging inspection, P(D), can include inspecting lot and date codes on the package and inspecting package materials. The external visual inspection, P(E), can include inspecting for:

evidence of resurfacing or remarking;
the number of correct leads;
contaminants indicative of used, scrapped, or reworked items;
the size and shape of solder spheres;
discoloration of color between devices within a lot;
difference in front, logo, or marking location within the lot;
previous visible markings;
different backside markings within the lot;
color or texture variations; and
verification of country or origin within the lot.

The dimensional inspection, P(F), can include a comparison against device drawings and data sheet dimensions. The ANN 226 uses the fuzzy logic unit 228 to output fuzzy AOI inspection accuracy percentages for the P(E) external visual inspection in block 618 and output fuzzy AOI inspection accuracy percentages for the P(F) dimensional inspection in block 620. In block 622, the analysis system 110 combines the outputs from each step to determine whether further testing is required. For example, the analysis system 110 can combine the outputs according to Equation 1:

$$P(A)+P(B)+P(C)+P(D)+P(E)+P(F)=P^* \qquad (1)$$

The analysis system 110 determines whether testing is complete, additional testing is required, or the electronic component 202a-202n is a suspected non-conforming item. For example, if $P^*=P(X)=75\sim100$, then testing may be completed. If $P^*=P(Y)=50\sim75$, additional next-level testing may be required. If $P^*=P(Z)<50$, testing may have failed, and the electronic component 202a-202n can be suspected as counterfeit or otherwise non-conforming. The output of each phase could be one of P(X), P(Y), or P(Z), where P(X) may mean "does not appear to be non-conforming (e.g., counterfeit)", P(Y) may mean inconclusive (i.e., undetermined), and P(Z) may mean the component "appears to be non-conforming." In some embodiments, the output from each step is displayed via the display interface 112, and multiple output values and a summary can be presented prior to or with a predicted outcome. In some embodiments, the analysis system 110 collects and displays, via the display interface 112, all AOI images and incorporates the images into a final report.

If the analysis system 110 determines that additional testing is required ($P^*=P(Y)$), the "tier two" algorithm 604 can be executed to perform the next-level testing as shown in FIG. 6C. The analysis system 110 can perform component inspection by performing marking permanency P(G), internal visual inspection P(H), electrical testing P(I), and radiographic inspection P(L). The marking permanency P(L) can include an application of one or more chemicals or solvents followed by a scrape test to determine a permanency of a marking. The internal visual inspection P(H) can include a determination regarding a die feature size, configuration cross sample, die mask analysis, and inspection of integrated circuits including glass body diodes and transistor/power diodes. The electrical testing P(I) can include parametric testing, such as at 25° C., on integrated circuits and hybrids and on diodes and transistors. The radiographic testing P(L) can include evaluating variations in the homogeneity consistency and uniformity and performed using an X-ray imaging system and method. The radiographic testing P(L) can include an EDS analysis on the integrated circuits and hybrids and on diodes and transistors.

The ANN 226 outputs binary values based on the permanency markings in block 624, outputs binary values based on the internal visual inspection in block 626, outputs binary values based on the electrical testing in block 628, and outputs binary values based on the radiographic inspection in block 630. In block 632, the analysis system 110 combines the outputs from each step to determine whether further testing is required. For example, the analysis system 110 can combine the outputs according to Equation 2:

$$P(G)+P(H)+P(I)+P(L)=P^{**} \qquad (2)$$

The analysis system 110 determines whether testing is complete, additional testing is required, or the electronic component 202a-202n is a suspected non-conforming item. For example, if $P^{}=P(X)$, then testing can be completed. If $P^{}=P(Y)$, additional next-level testing can be required. If $P^{}=P(Z)$, testing may have failed, and the electronic component 202a-202n may be suspected as non-conforming. The output of each phase is one of P(X), P(Y), or P(Z). In some embodiments, the output from each step is displayed via the display interface 112, and multiple output values and a summary can be presented prior to or with a predicted outcome. In some embodiments, the analysis system 110 collects and displays, via the display interface 112**, all AOI images and incorporates the images into a final report.

If the analysis system 110 determines that additional testing is required ($P^{}=P(Y)$), the "tier three" algorithm 606 can be executed to perform the next-level testing as shown in FIG. 6D. The analysis system 110** can perform component inspection by performing solderability testing P(J), lead finish inspection P(K), and software verification P(M). Solderability testing P(J) can evaluate whether the solderability requirements are being met. The lead finish P(K) can include evaluating variations in the lead finish between parts. The software verification testing P(M) can determine whether a miss-match between reported and documented firmware exists, determine self-tests and functionality failures associated with embedded firmware, and determine whether there is a failure of an item to accept and execute OM software.

The ANN 226 outputs binary values based on the solderabilty testing in block 634, outputs binary values based on the lead finish compliance in block 636, and outputs binary values based on the software verification in block 638. In block 640, the analysis system 110 combines the outputs from each step to determine whether further testing is required. For example, the analysis system 110 can combine the outputs according to Equation 3:

$$P(I)+P(K)+P(M)=P^{***} \qquad (3)$$

The analysis system 110 determines whether testing is complete, human inspection is required, or the electronic component 202a-202n is a suspected non-conforming item.

For example, if P*=P(X), then testing can be completed. If P*=P(Y), additional testing by a human operator may be required. If P***=P(Z), testing may have failed, and the electronic component 202a-202n can be suspected as non-conforming. The output of each phase is one of P(X), P(Y), or P(Z). In some embodiments, the output from each step is displayed via the display interface 112, and multiple output values and a summary can be presented prior to or with a predicted outcome. In some embodiments, the analysis system 110 collects and displays, via the display interface 112, all AOI images and incorporates the images into a final report.

In some embodiments, the analysis system 110 is configured to employ three decision matrices to test various characteristics of a product/component. In the first decision matrix, the ANN 226 within the analysis system 110 can employ Equation (1) to analyze various characteristics of a product/component to determine whether to continue with other testing. In the second decision matrix, the ANN 226 within the analysis system 110 can employ Equation (2) to analyze additional characteristics of the product/component to determine whether to continue with other testing. In the third decision matrix, the ANN 226 within the analysis system 110 can employ Equation (3) to analyze additional characteristics of the product/component to determine whether to continue with other means of testing, such as human testing.

In some embodiments, the analysis system 110 could analyze the following characteristics of an electronic component under inspection:
  the size of the electronic component;
  the location of a "pin 1" marker on the electronic component;
  the dimple size of the "pin 1" marker on the electronic component;
  the size of text characters on the electronic component;
  the font of text characters on the electronic component;
  the spacing between text characters on the electronic component;
  the position of text characters on the electronic component with respect to a known location (such as the "pin 1" location);
  the straightness or perpendicularity of mold lines; and
  the surface finish or roughness of molded surfaces.
For example, the analysis system 110 can perform pattern matching using the logo on the electronic component to known good logos of the same manufacturer. In addition, the analysis system 110 could analyze the following characteristics of the electronic component under inspection (assuming the electronic component can be flipped):
  the uniformity of solder plating on the electronic component;
  the uniformity of interfaces of solder interconnects to the body of the electronic component;
  the flatness of the solder leads on the electronic component; and
  the quality of lead ends of the electronic component.
Any single one of these features or any combination of these features could be analyzed by the ANN 226, using the fuzzy logic unit 228, to determine whether the electronic component 202a-202n is counterfeit. As noted above, the algorithms created or selected could be based on the type of electronic component, the positioning accuracy requirements of the electronic component, the image capture speed or field of view of any imaging device used to image the electronic component, the packaging of the electronic component, or other factors.

In this way, the conditional framework 600 supports a suite of image processing algorithms to perform comparative analysis via different testing processes of various features that uniquely distinguish conforming and non-conforming products, such as authentic and counterfeit components. The algorithms employed by the ANN 226 can provide results in the form of pass/fail/inconclusive indicators, which indicate whether non-conformance is suspected for a single component or a group of components. The overall pass/fail/inconclusive indicator for a component could be based on statistical variances within a lot (without use of a reference part), a comparison of the component's characteristic(s) to one or more reference parts, or a comparison of the component's characteristic(s) to dimensions or tolerances of manufacturer. The system 100 could use the marking system 230 to mark or otherwise identify non-conforming components. The suite of algorithms used here provides a robust blend of target discriminators that distinguish between authentic and counterfeit components based on particular features that represent potential signatures evidencing counterfeiting.

In some embodiments, different features can be weighted differently during the analysis of an electronic component when generating a pass/fail/inconclusive indicator. For example, statistical weightings could be used across all features of interest, and the weights could vary in relation to different components or different tiers of testing. As a particular example, features that are easier to counterfeit may be given less weight since similarity between authentic and counterfeit components is easier to achieve. In contrast, features that are harder to counterfeit may be given more weight since similarity between authentic and counterfeit components is harder to achieve. Mathematically, this approach can be represented as a weighted partial least squares (wPLS) problem, where the weights on the inputs are determined by criteria such as historical variation in the accuracy with which the input parameters may be determined. In this formalism, the number of weighted inputs can be much larger than the number of outputs, and component acceptability can be determined by comparison to a metric for each output variable.

Also, in some embodiments, a confidence level can be associated with a pass/fail/inconclusive indicator or a different tier of testing. The confidence level can identify how confident the analysis system 110 is in its determination that a component is or is not counterfeit. The confidence level could be calculated in any suitable manner. For example, the confidence level could be based on the size of the lot of components being inspected, where inspections of larger lots may lead to higher confidence levels. The confidence level could also be based on the number of "golden" or reference components used in an inspection, where inspections made with reference to more reference components may lead to higher confidence levels.

Note that before placing a system 100 into use, the system 100 can be calibrated and trained. Calibration of a system 100 can involve identifying current illumination, image capture, or other features of the system 100. For example, one or more known calibration tiles or other objects could be illuminated by the system 100, and one or more images or other data associated with the calibration tiles or other objects could be analyzed. Based on the analysis results, changes could be made to the illumination or image capture mechanisms, correction factors could be applied to calculations performed by the system 100, or other actions could occur so that the determined characteristics of the calibration tiles or other objects match the known characteristics of the calibration tiles or other objects. However, any other suitable technique could be used to calibrate a system 100.

Training of the ANN 226, using the fuzzy logic unit 228, in the system 100 generally refers to the identification of information to be used when analyzing a component being inspected. For example, the training could include identifying a "signature" of known good reference components. In some circumstances, a known good signature can be obtained by scanning known good components with a calibrated system 100. The signature could be uploaded to the database 306 for later use or for use by other system 100. The training could be controlled by a software program executed by the system 100, where the software program automatically controls the number of requisite "good" reference samples and test orientations and subsequently defines the limits of acceptance. Note, however, that training may not be necessary or may be minimized if a known good signature can be obtained, such as from the one or more databases 306.

Although FIG. 6 illustrates one example of a conditional framework 600 for selecting one or more algorithms to be used for screening electronic components, various changes may be made to FIG. 6. For example, any number of "tier one," "tier two," and "tier three" algorithms could be supported. Also, additional levels of algorithms could also be supported. For instance, a fourth tier could be used to more thoroughly test electronic components that fail the tier three tests or that are on the border of failing the tier three tests. The "level four" algorithms could involve more detailed analyses or analyses in different spectrums, such as X-ray or XRF analyses. Further, the deterministic automated selection of algorithms can be calibrated and trained as described above.

Figure 7:
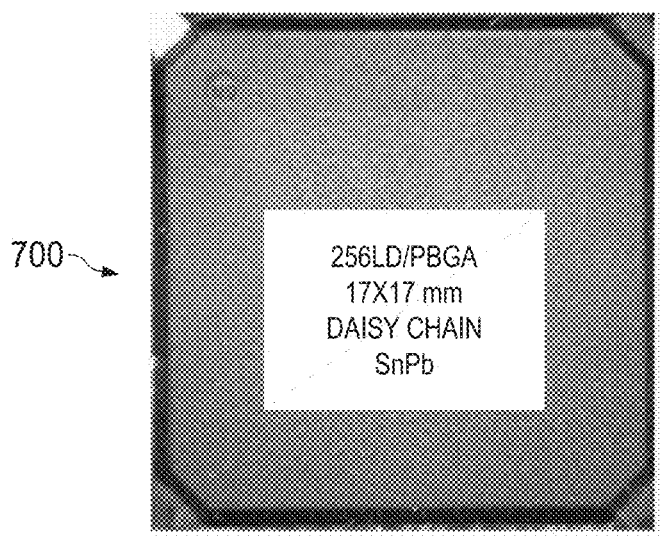
FIGS. 7 through 9 illustrate example data collected by an inspection station according to this disclosure.
Figure 8:
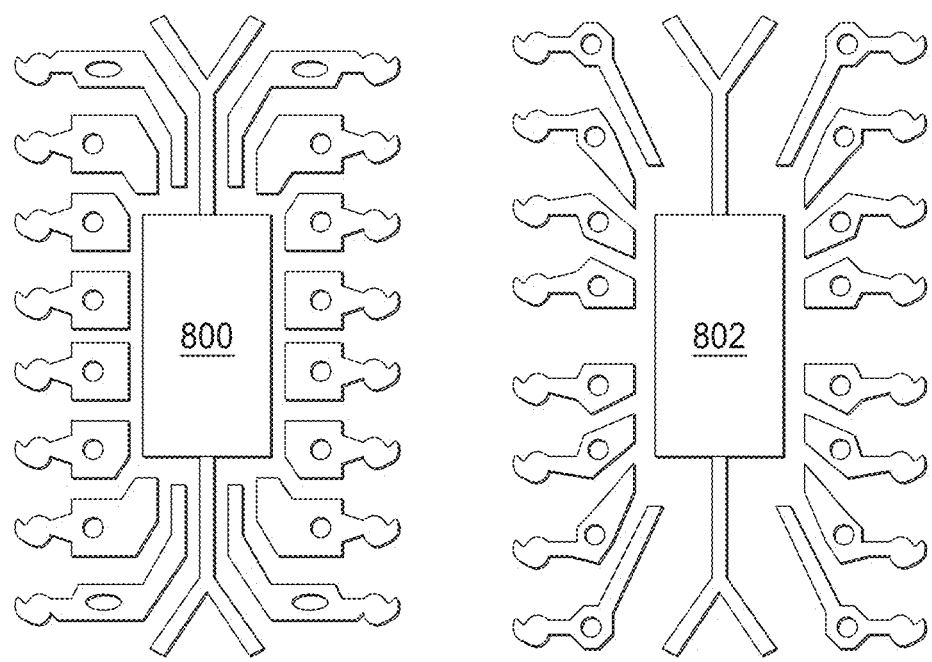
Figure 9:
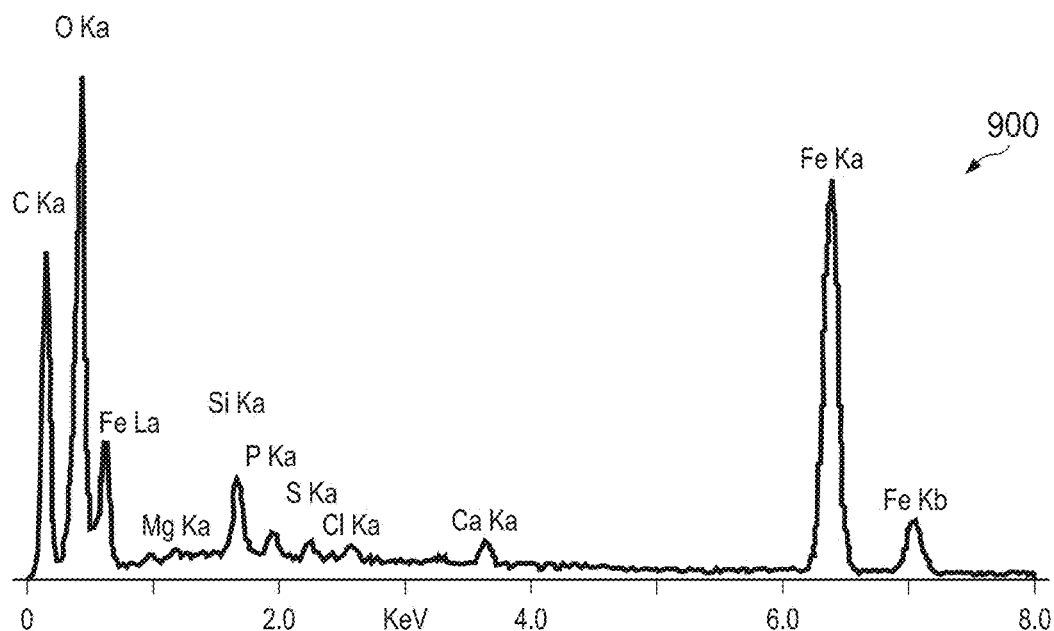

FIGS. 7 through 9 illustrate example data collected by an inspection station according to this disclosure. FIG. 7 illustrates an example visible-light image 700 of an electronic component under test. As shown in FIG. 7, the image 700 captures an integrated circuit chip, along with one or more of the chip's associated leads. The image 700 also captures text printed or engraved onto the chip (possibly including a logo of the chip's manufacturer not shown here) and a "pin 1" dimple in the upper left corner of the chip. As described below, any of these features or any combination of these features can be analyzed to determine whether the integrated circuit chip captured in the image 700 is authentic or counterfeit.

FIG. 8 illustrates example low-power X-ray scans 800-802 of different integrated circuit chips. As can be seen here, the scans 800-802 indicate that the integrated circuit chips have different metallic structures inside the chips. The X-ray scan of a chip can therefore be compared (either to a known good component or another component in the same lot or to the typical variation from chip to chip) to determine whether counterfeiting is suspected.

FIG. 9 illustrates an example XRF spectrographic plot 900 identifying the elemental composition of an integrated circuit chip. As can be seen here, the plot 900 contains various spikes having different amplitudes in different locations. The spikes and their amplitudes identify the composition of an integrated circuit chip. Comparing different plots for different integrated circuit chips can help to identify whether the different integrated circuit chips have the same/similar elemental composition.

Data such as that shown in FIGS. 7 through 9 could be generated by the imaging system 106 and provided to the analysis system 110. The analysis system 110 could analyze this data, such as via comparisons with data for reference components or comparisons to components within the same lot, to identify potentially counterfeit items.

Although FIGS. 7 through 9 illustrate examples of data collected by an inspection station, various changes may be made to FIGS. 7 through 9. For example, the image, X-ray scans, and XRF spectrographic plots shown here are examples only, and other electronic components would have their own images, X-ray scans, and XRF spectrographic plots. Also, other or additional types of data could be generated by the imaging system 106 and analyzed by the analysis system 110.

Figure 10:
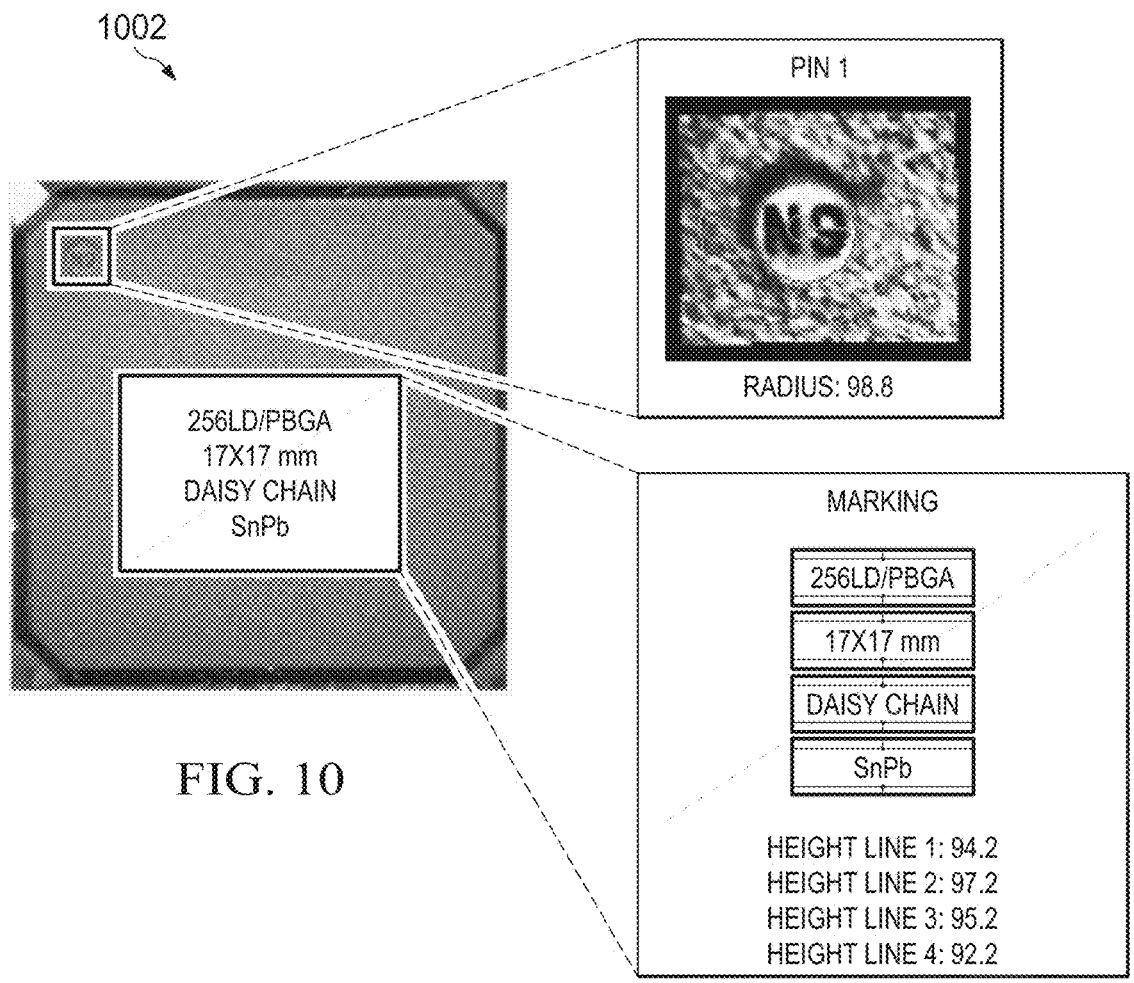

FIGS. 10 through 12 illustrate example analysis results associated with electronic components according to this disclosure. In FIG. 10, an image 1002 of a component is analyzed to identify the radius of a "pin 1" marker and a height of various text on the component. The characteristics of counterfeit components can differ significantly from the characteristics of authentic components, allowing the system 100 to identify the counterfeit item.

In FIG. 11, an example report 1100 contains analysis results for multiple electronic components. The report 1100 summarizes analysis results, such as those shown in FIG. 10, for easy review. The report 1100 provides baseline and areas of improvement based on using this technique for AOI counterfeit inspection. Even without reference to any known good components, the inspection station 100 could flag a subset or all of these electronic components as being counterfeit.

In FIG. 12, an example estimation report 1200 contains analysis results for multiple electronic components. The report 1200 summarizes a number of hours estimated per tier and a number of hours estimated for all the tiers combined.

Although FIGS. 10 through 12 illustrate examples of analysis results associated with electronic components, various changes may be made to FIGS. 10 through 12. For example, analysis results generated by the system 100 could be used in any other suitable manner As a particular example, analysis results could be uploaded to the one or more databases 306 for storage and later use.

Figure 13:
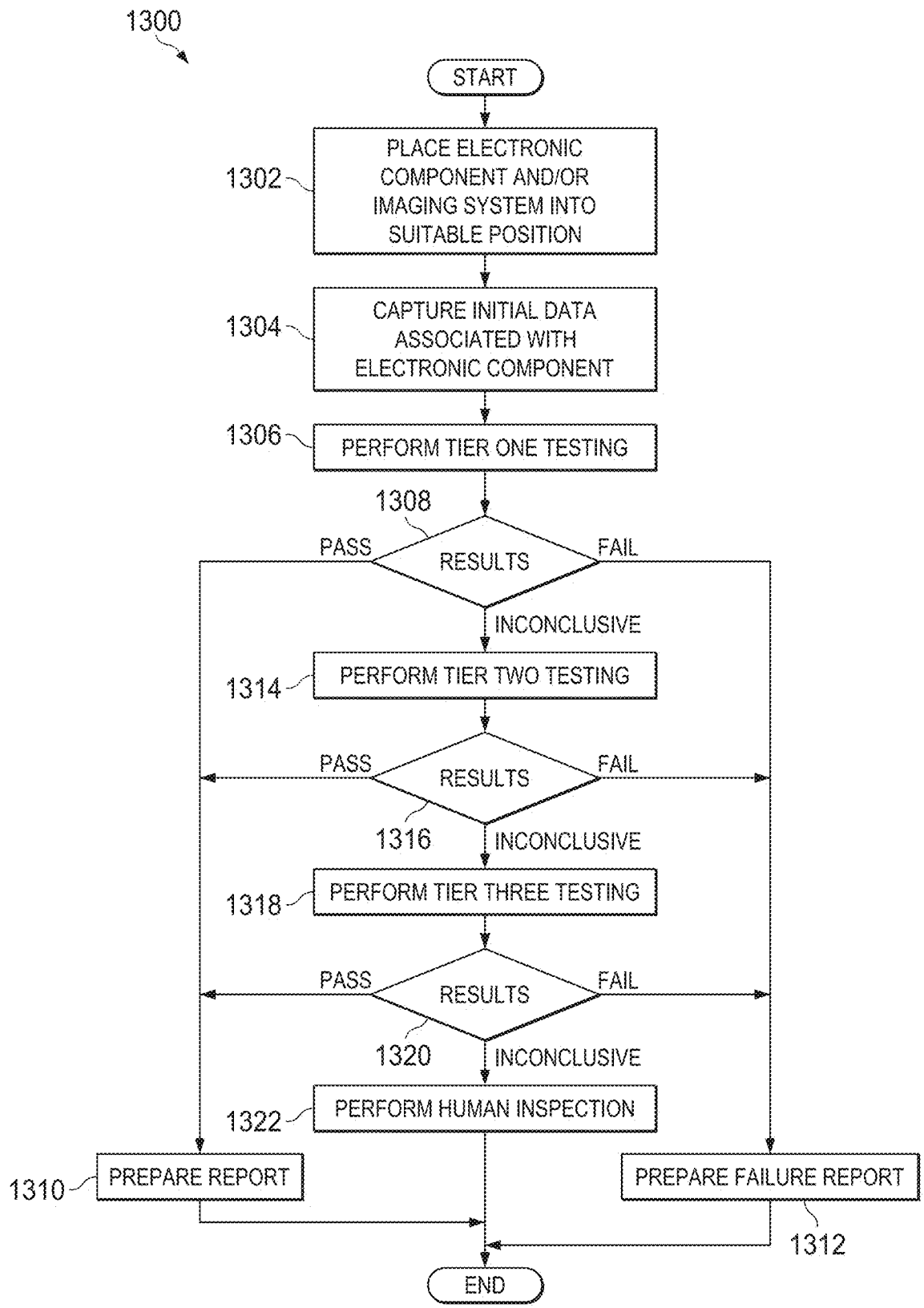
FIG. 13 illustrates an example method for screening electronic components to detect counterfeit articles according to this disclosure.

FIG. 13 illustrates an example method 1300 for screening electronic components to detect counterfeit articles according to this disclosure. For ease of explanation, the method 1300 is described with respect to the system 100 of FIGS. 1 and 2 operating in the system 300 of FIG. 3. However, the method 1300 could be used by any suitable device and in any suitable system.

As shown in FIG. 13, an electronic component or an imaging system is placed into a suitable position at step 1302, and initial data associated with the electronic component is captured at step 1304. This could include, for example, placing the electronic component into a suitable position using the transport system 220 or moving the imaging system 106 using the translation system 222. The imaging system 106 could capture any suitable data associated with the electronic component, such as one or more images, X-ray scans, or XRF spectrographic measurements.

The analysis system 110 performs "tier one" testing to determine whether the component is authentic at step 1306. This could include, for example, the analysis system 110 receiving a number of inputs including a type of component being tested, a number of potential components being inspected, a part number of the component being tested, and a manufacturer of the component. This could also include reviewing documentation and obtaining information from one or more databases 306. One or more characteristics of each electronic component can be identified by performing packaging inspection, external visual inspection, and dimensional inspection. Note that this step could include analyzing the initial data collected during step 1302 or collecting additional data about each electronic component.

The determined characteristics of the electronic component are compared to characteristics of other components or to characteristics of one or more known good components during the step 1306. Based on the comparison, a determination is made whether the electronic component is non-conforming, such as potentially counterfeit, at step 1308. This could include, for example, the analysis system 110 identifying variations in the same characteristic across multiple electronic components in a lot. This could also include the analysis system 110 comparing characteristics of the electronic components being inspected to corresponding characteristics of one or more reference components. Different characteristics could be weighted differently, and a pass/fail/inconclusive indicator or other value could be generated to indicate whether a counterfeited item has been detected. As noted above, a confidence level can be associated with each pass/fail/inconclusive indicator to identify the amount of confidence in the counterfeit decision. If the tier one test results in a conforming product ("pass"), the analysis system 110 provides a summary report at step 1310, and the process ends. If the tier one test results in a non-conforming determination ("fail"), the analysis system 110 provides a failure report at step 1312 and optionally marks the component as non-conforming or counterfeit, and the process ends.

If the results of the tier one test are inconclusive, the analysis system 110 proceeds to tier two testing. The analysis system 110 performs the tier two testing to determine whether the component is authentic at step 1314. This could include, for example, the analysis system 110 performing more detailed analysis. One or more characteristics of each electronic component are identified, such as by performing marking permanency P(G), internal visual inspection P(H), electrical testing P(I), and radiographic inspection P(L) testing. The analysis system 110 could analyze images, X-ray scans, or XRF spectrographic measurements to identify various characteristics of each electronic component. Example characteristics could include any individual feature or combination of features described above.

The determined characteristics of the electronic component are compared to characteristics of other components or to characteristics of one or more known good components during the step 1314. Based on the comparison, a determination is made whether the electronic component is non-conforming, such as potentially counterfeit. This could include, for example, the analysis system 110 identifying variations in the same characteristic across multiple electronic components in a lot. This could also include the analysis system 110 comparing characteristics of the electronic components being inspected to corresponding characteristics of one or more reference components. Different characteristics could be weighted differently, and a pass/fail/inconclusive indicator or other value could be generated to indicate whether a counterfeited item has been detected. Weighting values different from tier one can be applied in tier two. As noted above, a confidence level can be associated with each pass/fail/inconclusive indicator to identify the amount of confidence in the counterfeit decision.

A determination is made as to whether the component is conforming or non-conforming or if the tier two test was inconclusive at step 1316. If the tier two test results in a conforming product ("pass"), the analysis system 110 provides a summary report at step 1310, and the process ends. If the tier two test results in a non-conforming determination ("fail"), the analysis system 110 provides a failure report at step 1312 and optionally marks the component as non-conforming or counterfeit, and the process ends.

If the results of the tier two test are inconclusive, the analysis system 110 proceeds to tier three testing. The analysis system 110 performs the tier three testing to determine whether the component is authentic at step 1318. This could include, for example, the analysis system 110 performing a higher level of testing. One or more characteristics of each electronic component can be identified, such as by performing solderability testing, lead finish inspection, and software verification scans. Example characteristics could include any individual feature or combination of features described above.

The determined characteristics of the electronic component are compared to characteristics of other components or to characteristics of one or more known good components during the step 1320. Based on the comparison, a determination is made whether one or more of the electronic components are non-conforming, such as potentially counterfeit. This could include, for example, the analysis system 110 identifying variations in the same characteristic across multiple electronic components in a lot. This could also include the analysis system 110 comparing characteristics of the electronic components being inspected to corresponding characteristics of one or more reference components. Different characteristics could be weighted differently, and a pass/fail/inconclusive or other value could be generated to indicate whether a counterfeited item has been detected. Weighting values different from tier one and/or tier two can be applied in tier three. As noted above, a confidence level can be associated with each pass/fail/inconclusive to identify the amount of confidence in the counterfeit decision.

If the tier three test results in a conforming product ("pass"), the analysis system 110 provides a summary report at step 1310, and the process ends. If the tier three test results in a non-conforming determination ("fail"), the analysis system 110 provides a failure report at step 1312 and optionally marks the component as non-conforming or counterfeit, and the process ends. If the results of the tier three testing are inconclusive, the analysis system 110 can proceed to human inspection or additional higher-tier testing at step 1322.

The results of the analysis could be used in any suitable manner For example, any component determined to be potentially counterfeit could be marked. Results from one or more of the stages can be saved for use in future analysis operations. That is, the analysis system can use previous testing results to develop algorithms and inspections values, such as weighting values and confidence levels, for use in later inspections. The marking could take any suitable form, such as a visible marking on the component. Authentic components could be provided for use, while the counterfeit components could be pulled from a lot. Reports could be also be generated, and analysis results could be uploaded to a database 306 or other location for storage and later use.

Although FIG. 13 illustrates one example of a method 1300 for screening electronic components to detect counterfeit articles, various changes may be made to FIG. 13. For example, while shown as a series of steps, various steps in FIG. 13 could overlap, occur in parallel, occur in a different order, or occur multiple times. As a particular example, characteristics of each electronic component being inspected could be compared to characteristics of one or more known good components while each electronic component is being imaged. Once all electronic components in a lot have been imaged, characteristics of the electronic components being inspected can be compared against each other.

Combining an automated optical inspection methodology with the ability to identify counterfeit parts can drastically improve quality with the reassurance that specific parts allocated for programs meet all necessary requirements. Current inspection procedures are subject to human error due to sampling a handful of parts and reporting on the findings. The systems are able to visually inspect every part (if necessary) arriving at one or more locations and provide a reassurance that no parts will be counterfeit.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
obtaining, by an automated optic inspection (AOI) system, data associated with an electronic component; and
conducting, by the AOI system, a multi-tier inspection process comprising at least three tiers to verify a conformance of the electronic component, wherein each of the tiers comprises a different type of identification test, wherein at least one of the tiers is configured to provide fuzzy outputs;
wherein the multi-tier inspection process comprises:
analyzing, by the AOI system, the data associated with the electronic component using multiple first tests associated with a first tier of the multi-tier inspection process to determine whether the electronic component conforms to a pre-specified requirement, wherein the multiple first tests associated with the first tier comprise an automated packaging inspection, an automated external visual inspection, and an automated dimensional inspection, wherein a separate input value is generated for each of the multiple first tests;
generating an output based on the analysis, wherein the output is based on an equation that uses the separate input value for each of the multiple first tests; and
determining, by the AOI system, whether additional testing that uses one or more next-level tests associated with at least a second tier of the multi-tier inspection process is required.

2. The method of claim 1, wherein determining whether additional testing is required comprises:
identifying, based on the output, whether the electronic component is likely a non-conforming component, a conforming component, or undetermined.

3. The method of claim 1, wherein:
the second tier includes at least one of: marking permanency testing, internal visual inspection, electrical testing, and radiographic inspection; and
a third of the tiers of the multi-tier inspection process includes inspecting for at least one of: lead finish compliance, solderability testing, and software verification.

4. The method of claim 1, wherein:
obtaining the data associated with the electronic component comprises obtaining data associated with images of multiple electronic components captured using an imaging system; and
the method further comprises at least one of:
moving each electronic component into a position for imaging by the imaging system; and
moving the imaging system into a position for imaging of each electronic component.

5. The method of claim 1, wherein:
analyzing the data associated with the electronic component comprises calculating a pass/fail/inconclusive value for the electronic component, the pass/fail/inconclusive value based on multiple characteristics of the electronic component; and the method further comprises weighting different characteristics of the electronic component with different weights when calculating the pass/fail/inconclusive value.

6. The method of claim 1, further comprising:
obtaining one or more characteristics of at least one reference component or at least one previously-tested component from at least one database, the at least one database configured to provide characteristics associated with multiple reference components or multiple previously-tested components; and
comparing the data associated with the electronic component against the one or more characteristics of the at least one reference component or the at least one previously-tested component.

7. The method of claim 1, wherein obtaining the data associated with the electronic component comprises obtaining at least one of:
an optical image of the electronic component;
an infrared or X-ray scan of the electronic component; and
an X-ray fluorescence (XRF) spectrographic measurement of the electronic component.

8. The method of claim 1, wherein the identification test for at least one of the tiers comprises an algorithm that identifies one or more characteristics of the electronic component, the one or more characteristics including at least one of:
one or more characteristics of markings on the electronic component, the markings including at least one of: a logo, text, and a pin marker;
one or more characteristics of a molded surface of the electronic component;
one or more dimensions of the electronic component; and
one or more characteristics of solder leads of the electronic component.

9. The method of claim 1, wherein determining whether additional testing is required comprises determining whether additional testing is required automatically without human intervention.

10. An apparatus comprising:
at least one memory configured to store data associated with an electronic component; and
at least one processing device configured to:
obtain the data associated with the electronic component; and
conduct a multi-tier inspection process comprising at least three tiers to verify a conformance of the electronic component, wherein each of the tiers comprises a different type of identification test, wherein at least one of the tiers is configured to provide fuzzy outputs;
wherein, to conduct the multi-tier inspection process, the at least one processing device is configured to:
analyze the data associated with the electronic component using multiple first tests associated with a first tier of the multi-tier inspection process to determine whether the electronic component conforms to a pre-specified requirement, wherein the multiple first tests associated with the first tier comprise an automated packaging inspection, an automated external visual inspection, and an automated dimensional inspection, wherein the least one processing device is configured to generate a separate input value for each of the multiple first tests;
generate an output based on the analysis, wherein the output is based on an equation that uses the separate input value for each of the multiple first tests; and
determine whether additional testing that uses a process associated with at least a second tier of the multi-tier inspection process is required.

11. The apparatus of claim 10, wherein, to determine whether additional testing is required, the at least one processing device is configured to:
identify, based on the output, whether the electronic component is likely a non-conforming component, a conforming component, or undetermined.

12. The apparatus of claim 10, wherein:
the first tier comprises an automated optical inspection;
the second tier comprises at least one of: marking permanency testing, internal visual inspection, electrical testing, and radiographic inspection; and
a third of the tiers comprises inspecting for at least one of: lead finish compliance, solderability testing, and software verification.

13. The apparatus of claim 10, further comprising:
an imaging system configured to capture data associated with multiple electronic components; and
at least one of:
a transport system configured to move each electronic component into a position for imaging by the imaging system; and
a translation system configured to move the imaging system into a position for imaging of each electronic component.

14. The apparatus of claim 13, wherein the imaging system comprises a telecentric imaging system.

15. The apparatus of claim 10, wherein:
the at least one processing device is configured to calculate a pass/fail/inconclusive value for the electronic component based on multiple characteristics of the electronic component; and
different characteristics of the electronic component are associated with different weights.

16. The apparatus of claim 10, wherein the at least one processing device is configured to obtain at least one of:
an optical image of the electronic component;
an infrared or X-ray scan of the electronic component; and
an X-ray fluorescence (XRF) spectrographic measurement of the electronic component.

17. The apparatus of claim 10, wherein the identification test for at least one of the tiers of the multi-tier inspection process comprises an algorithm that identifies one or more characteristics of the electronic component, the one or more characteristics including at least one of:
one or more characteristics of markings on the electronic component, the markings including at least one of: a logo, text, and a pin marker;
one or more characteristics of a molded surface of the electronic component;
one or more dimensions of the electronic component; and
one or more characteristics of solder leads of the electronic component.

18. The apparatus of claim 10, wherein the at least one processing device is configured to determine whether additional testing is required automatically without human intervention.

19. The apparatus of claim 10, wherein the at least one processing device is configured to use an automated neural network and fuzzy logic.

20. A non-transitory computer readable medium containing instructions that, when executed by at least one processing device, cause the at least one processing device to:
    obtain data associated with an electronic component; and
    conduct a multi-tier inspection process comprising at least three tiers to verify a conformance of the electronic component, wherein each of the tiers comprises a different type of identification test, wherein at least one of the tiers is configured to provide fuzzy outputs;
    wherein, to cause the at least one processing device to conduct the multi-tier inspection process, the instructions when executed cause the at least one processing device to:
        analyze the data associated with the electronic component using multiple first tests associated with a first tier of the multi-tier inspection process to determine whether the electronic component conforms to a pre-specified requirement, wherein the multiple first tests associated with the first tier comprise an automated packaging inspection, an automated external visual inspection, and an automated dimensional inspection, wherein the instructions when executed cause the at least one processing device to generate a separate input value for each of the multiple first tests;
        generate an output based on the analysis, wherein the output is based on an equation that uses the separate input value for each of the multiple first tests; and
        determine whether additional testing that uses one or more next-level tests associated with at least a second tier of the multi-tier inspection process is required.

21. The non-transitory computer readable medium of claim 20, wherein the instructions that when executed cause the at least one processing device to determine whether additional testing is required comprise:
    instructions that when executed cause the at least one processing device to identify, based on the output, whether the electronic component is likely a non-conforming component, a conforming component, or undetermined.

22. The non-transitory computer readable medium of claim 20, wherein:
    the first tier includes an automated optical inspection;
    the second tier includes at least one of: marking permanency testing, internal visual inspection, electrical testing, and radiographic inspection; and
    a third of the tiers of the multi-tier inspection process includes inspecting for at least one of: lead finish compliance, solderability testing, and software verification.

23. A system comprising:
    handling equipment configured to position electronic components for inspection;
    imaging equipment configured to obtain data associated with each electronic component;
    scanning equipment configured to move at least one of the imaging equipment and the electronic components so that the imaging equipment is able to obtain the data associated with each electronic component; and
    an analysis system configured to:
        conduct a multi-tier inspection process comprising at least three tiers to verify an authenticity of the electronic components, wherein each of the tiers comprises a different type of identification test, wherein at least one of the tiers is configured to provide fuzzy outputs, wherein a first tier of the multi-tier inspection process includes multiple first tests, the multiple first tests comprising an automated packaging inspection, an automated external visual inspection, and an automated dimensional inspection, wherein the analysis system is configured to generate a separate input value for each of the multiple first tests; and
        analyze the data associated with the electronic components using fuzzy logic to determine whether each of the electronic components is conforming, wherein the data comprises an output that is based on an equation that uses the separate input values for each of the multiple first tests.

* * * * *